US008068987B2

(12) United States Patent
Afeyan et al.

(10) Patent No.: US 8,068,987 B2
(45) Date of Patent: Nov. 29, 2011

(54) METHOD AND SYSTEM FOR PROFILING BIOLOGICAL SYSTEMS

(75) Inventors: Noubar B. Afeyan, Lexington, MA (US); Jan van der Greef, Driebergen-Rijsenburg (NL); Frederick E. Regnier, W. Lafayette, IN (US); Aram S. Adourian, Woburn, MA (US); Eric K. Neumann, Lexington, MA (US); Matej Oresic, Espoo (FI); Elwin Robbert Verheij, Zeist (NL)

(73) Assignee: BG Medicine, Inc., Waltham, MA (US)

( * ) Notice: Subject to any disclaimer, the term of this patent is extended or adjusted under 35 U.S.C. 154(b) by 562 days.

(21) Appl. No.: 10/218,880

(22) Filed: Aug. 13, 2002

(65) Prior Publication Data

US 2003/0134304 A1 Jul. 17, 2003

Related U.S. Application Data

(60) Provisional application No. 60/312,145, filed on Aug. 13, 2001.

(51) Int. Cl.
*G01N 33/48* (2006.01)
*G01N 33/50* (2006.01)

(52) U.S. Cl. ............... 702/19; 703/2; 703/11; 707/706; 211/41.12; 436/173; 702/22

(58) Field of Classification Search ............ 702/19, 702/189; 703/2, 11
See application file for complete search history.

(56) References Cited

U.S. PATENT DOCUMENTS

| | | | |
|---|---|---|---|
| 5,644,503 A | 7/1997 | Ito et al. | |
| 6,194,217 B1 | 2/2001 | Matson | |
| 6,329,146 B1 * | 12/2001 | Crooke et al. | 435/6 |
| 6,615,141 B1 | 9/2003 | Sabry et al. | |
| 6,647,341 B1 | 11/2003 | Golub et al. | 702/19 |
| 6,656,695 B2 | 12/2003 | Berg et al. | 435/7.21 |
| 6,675,104 B2 | 1/2004 | Paulse et al. | 702/22 |
| 6,683,455 B2 | 1/2004 | Ebbels et al. | |
| 6,753,135 B2 | 6/2004 | Alters et al. | |
| 2002/0053545 A1 | 5/2002 | Greef | 210/656 |
| 2002/0095259 A1 | 7/2002 | Hood et al. | 702/19 |
| 2002/0095260 A1 * | 7/2002 | Huyn | 702/19 |
| 2002/0145425 A1 | 10/2002 | Ebbels et al. | |
| 2003/0004402 A1 | 1/2003 | Hitt et al. | |
| 2003/0023386 A1 | 1/2003 | Aranibar et al. | 702/19 |
| 2003/0040123 A1 | 2/2003 | Hastings | |
| 2003/0078739 A1 | 4/2003 | Norton et al. | |
| 2003/0111596 A1 | 6/2003 | Becker et al. | |
| 2003/0130798 A1 | 7/2003 | Hood et al. | 702/19 |
| 2003/0138827 A1 | 7/2003 | Kononen et al. | 435/6 |
| 2003/0143520 A1 | 7/2003 | Hood et al. | 435/4 |
| 2003/0229451 A1 | 12/2003 | Hamilton et al. | |
| 2004/0002842 A1 | 1/2004 | Woessner et al. | 703/11 |
| 2004/0018500 A1 | 1/2004 | Glassbrook et al. | |
| 2004/0018501 A1 | 1/2004 | Allen et al. | |
| 2004/0019429 A1 | 1/2004 | Coffin et al. | |
| 2004/0019430 A1 | 1/2004 | Hurban et al. | |
| 2004/0019435 A1 | 1/2004 | Winfield et al. | |
| 2004/0023295 A1 | 2/2004 | Hamilton et al. | |
| 2004/0024293 A1 | 2/2004 | Lawrence et al. | |
| 2004/0024543 A1 | 2/2004 | Zhang et al. | |
| 2004/0096917 A1 | 5/2004 | Ivey et al. | |
| 2004/0113062 A1 | 6/2004 | Norton | |
| 2004/0142496 A1 | 7/2004 | Nicholson et al. | |
| 2004/0214348 A1 | 10/2004 | Nicholson et al. | |
| 2004/0241743 A1 | 12/2004 | Nicholson et al. | |
| 2005/0037515 A1 | 2/2005 | Nicholson et al. | |
| 2005/0074745 A1 | 4/2005 | Clayton et al. | |
| 2005/0074834 A1 | 4/2005 | Chaplen et al. | |
| 2005/0130321 A1 | 6/2005 | Nicholson et al. | |

FOREIGN PATENT DOCUMENTS

| | | |
|---|---|---|
| WO | 97/18566 | 5/1997 |
| WO | 99/50437 | 10/1999 |
| WO | WO 00/47992 | 8/2000 |
| WO | WO 01/44269 A2 * | 6/2001 |
| WO | WO 01/92880 A2 | 12/2001 |
| WO | WO 02/052293 A1 | 7/2002 |
| WO | WO 02/085195 A2 | 10/2002 |
| WO | WO 02/086478 A2 | 10/2002 |
| WO | WO 02/086500 A2 | 10/2002 |
| WO | WO 02/086501 A2 | 10/2002 |
| WO | WO 02/086502 A2 | 10/2002 |
| WO | WO 02/099452 A1 | 12/2002 |
| WO | WO 03/017177 | 2/2003 |
| WO | WO 03/058238 A1 | 7/2003 |
| WO | WO 03/107270 A2 | 12/2003 |

OTHER PUBLICATIONS

"profile" definition, Merriam-Webster online dictionary, on the world wide web at http://www.m-w.com/cgi-bin/dictionary?book=Dictionary&va=profile, 2004, 1 page.*
Gribbestad et al., "Metabolite Composition in Breast Tumors Examined by Proton Nuclear Magnetic Resonance Stectroscopy," *Anticancer Research*, 19:1737-1746 (1999).
Holmes et al., "Chemometric Models for Toxicity Classification Based on NMR Spectra of Biofluids," *Chem. Res. Toxicol.*, 13:471-478 (2000).
Ideker et al., "A New Approach to Decoding Life: Systems Biology," *Annu. Rev. Genomics Hum. Genet.*, 2:343-372 (2001).
Ideker et al., "Integrated Genomic and Proteomic Analyses of a Systematically Perturbed Metabolic Network," *Science*, 292:929-934 (May 4, 2001).
Komoroski et al., "The Use of Nuclear Magnetic Resonance Spectroscopy in the Detection of Drug Intoxication," *Journal of Analytical Toxicology*, 24:180-187 (2000).

(Continued)

*Primary Examiner* — Carolyn L. Smith
(74) *Attorney, Agent, or Firm* — K&L Gates LLP

(57) ABSTRACT

The present invention provides methods and systems for developing profiles of a biological system based on the discernment of similarities, differences, and/or correlations between biomolecular components of a plurality of biological samples. Preferably, the method comprises utilizing hierarchical multivariate analysis of spectrometric data at one or more levels of correlation.

38 Claims, 21 Drawing Sheets

OTHER PUBLICATIONS

Nicholson et al., "'Metabonomics': understanding the metabolic reponses of living systems to pathophysiological stimuli via multivariate statistical analysis of biological NMR spectroscopic data," *Xenobiotica*, 29(11):1181-1189 (1999).

Tate et al., "Investigation of the Metabolite Variation in Control Rat Urine $^1$H NMR Spectroscopy," *Analytical Biochemistry*, 291:17-26 (2001).

Vogels et al., "Detection of Adulteration in Orange Juices by a New Screening Method Using Proton NMR Spectroscopy in Combination with Pattern Recognition Techniques," *J. Agric. Food Chem.*, 44:175-180 (1996).

Butte et al., "Discovering functional relationships between RNA expression and chemotherapeutic susceptibility using relevance networks," *PNAS*, 97(22):12182-12186 (2000).

Kose et al., "Visualizing plant metabolomic correlation networks using clique-metabolite matrices," *Bioinformatics*, 17(12):1198-1208 (2001).

Jellum et al, "Classification of Human Cancer Cells by Means of Capillary Gas Chromatography and Pattern Recognition Analysis," *Journal of Chromatography*, 217:231-237 (1981).

Oresic, "Systems Biology Mining of APO Lipoprotein Metabolic Pathways," *Proceedings of the 2$^{nd}$ International Conference on Systems Biology, ICSB 2001*, p. 113 (Nov. 2001).

Espina et al., "Detection of in vivo biomarkers of phospholipidosis using NMR-based metabonomic approaches," *Magnetic Resonance in Chemistry*, 39:559-565 (2001).

Holmes et al., "Development of a model for classification of toxin-induced lesions using $^1$H NMR spectroscopy of urine combined with pattern recognition," *NMR in Biomedicine*, 11:235-244 (1998).

Holmes et al., "The identification of novel biomarkers of renal toxicity using automatic data reduction techniques and PCA of proton NMR spectra of urine," *Chemometrics and Intelligent Laboratory Systems*, 44:245-255 (1998).

Lindon et aL, "Metabonomics: Metabolic Processes Studied by NMR Spectroscopy of Biofluids," *Concepts in Magnetic Resonance*, 12(5):289-320 (2000).

Lindon et al., "Pattern recognition methods and applications in biomedical magnetic resonance," *Progress in Nuclear Magnetic Resonance Spectroscopy*, 39:1-40 (2001).

Nicholls et al., "Metabonomic Investigations into Hydrazine Toxicity in the Rat," *Chem. Res. Toxicol.*, 14:975-987 (2001).

Nicholson et al., "Metabonomics: a platform for studying drug toxicity and gene function," *Nature Reviews*, 1:153-161 (2002).

Beecher, "Metabolomics: A New "Omics" Technology," *American Genomics/Proteomics Technology*, 4 pages (May/Jun. 2002).

Glassbrook et al., "Metabolic profiling on the right path," *Nature Biotechnology*, 18:1142-1143 (Nov. 2000).

\* cited by examiner

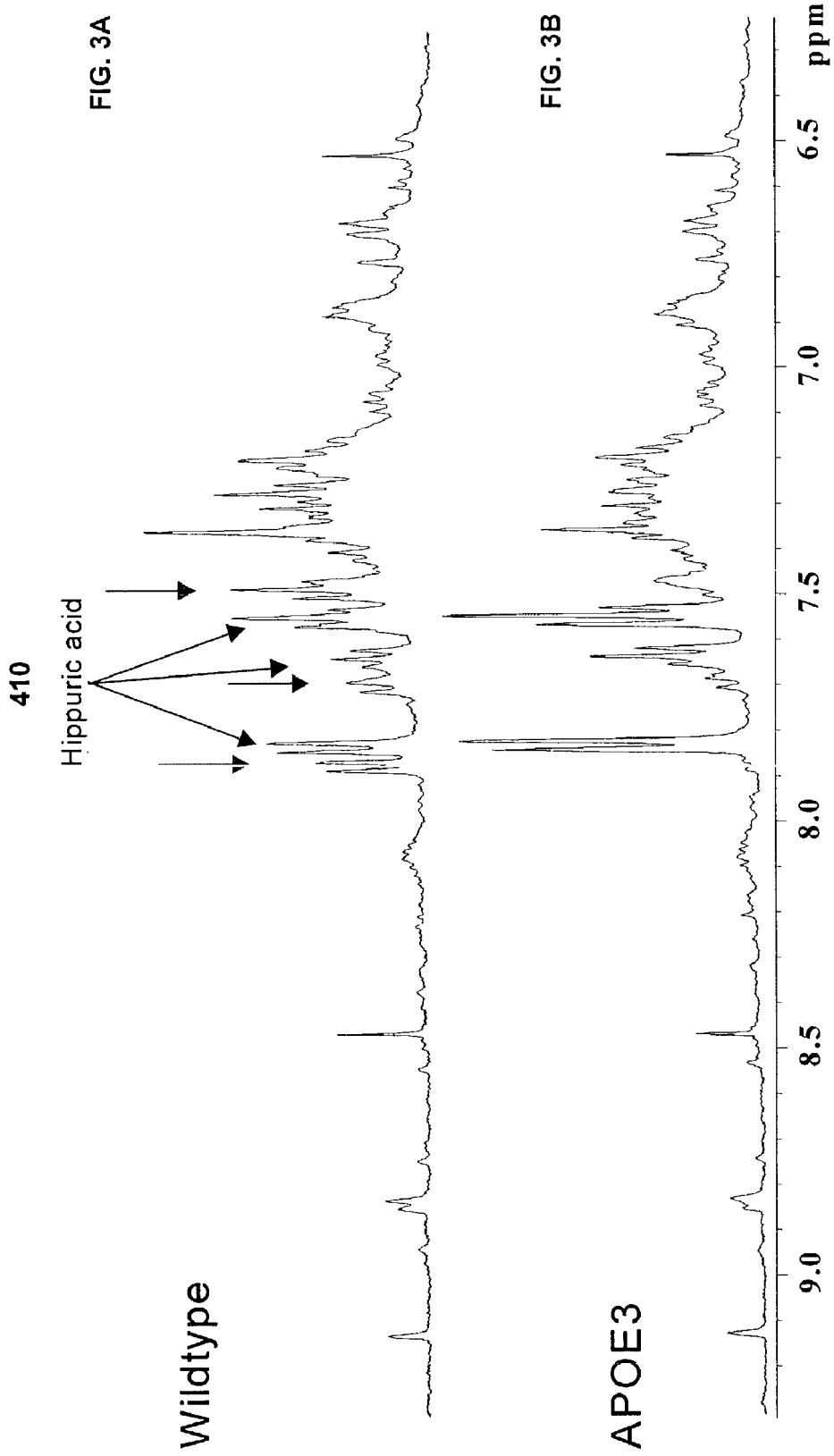

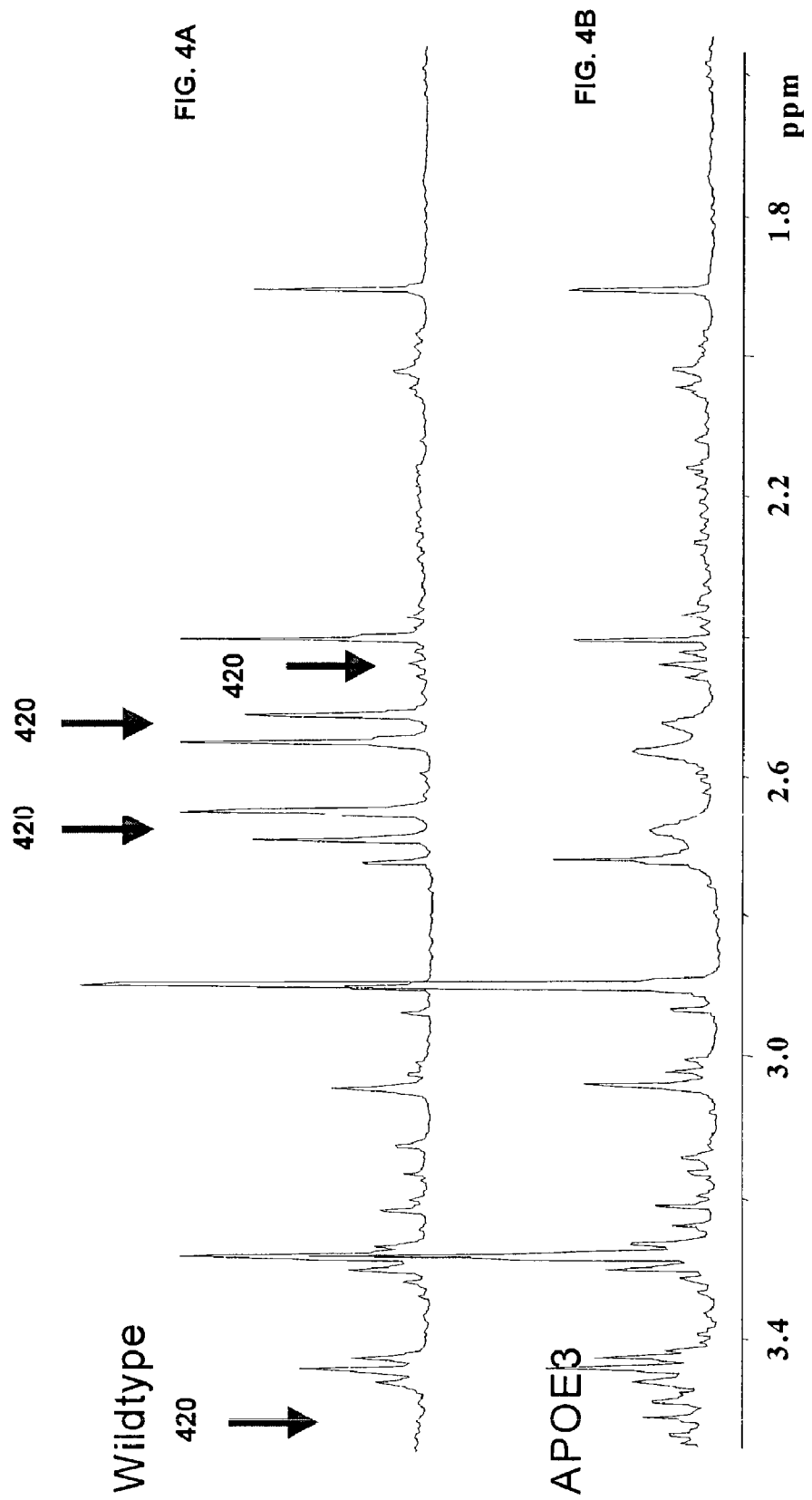

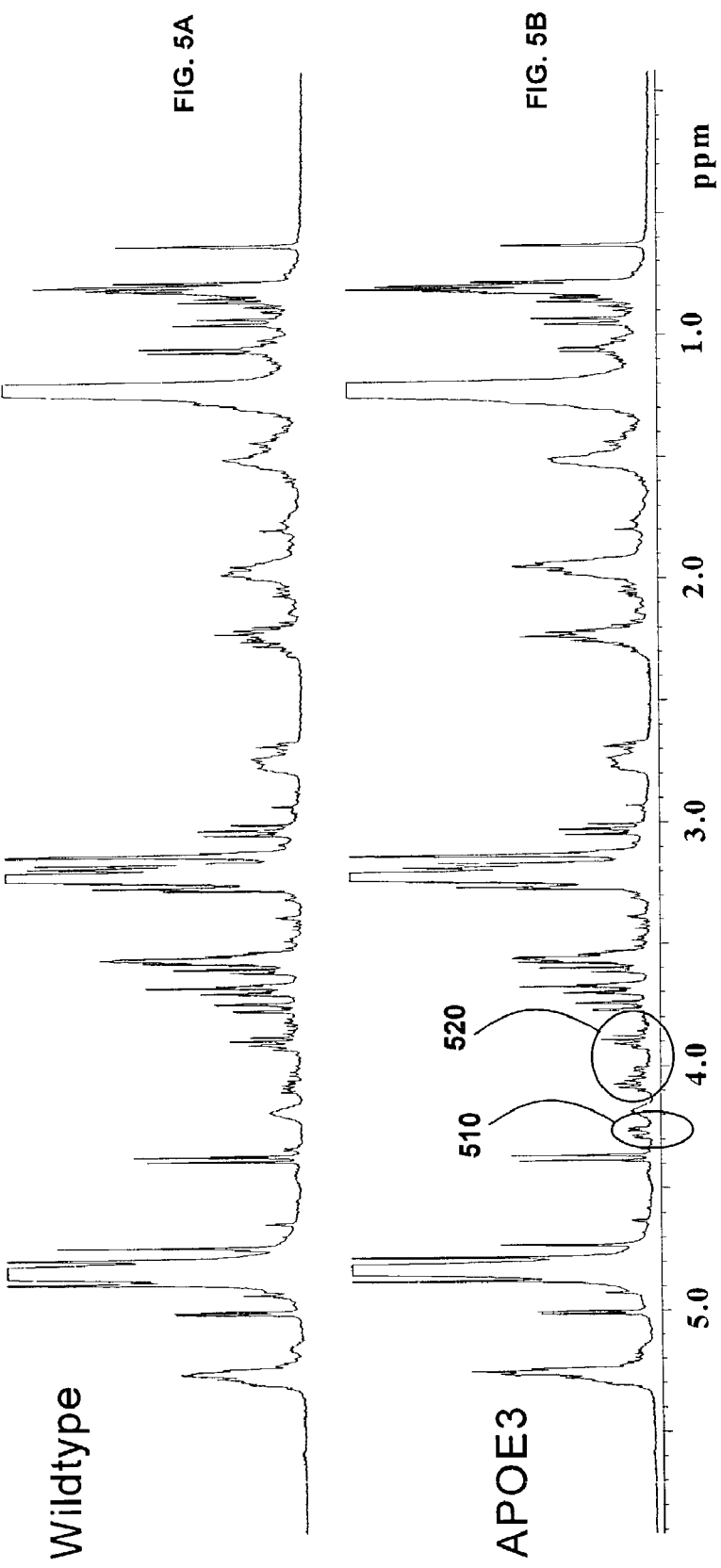

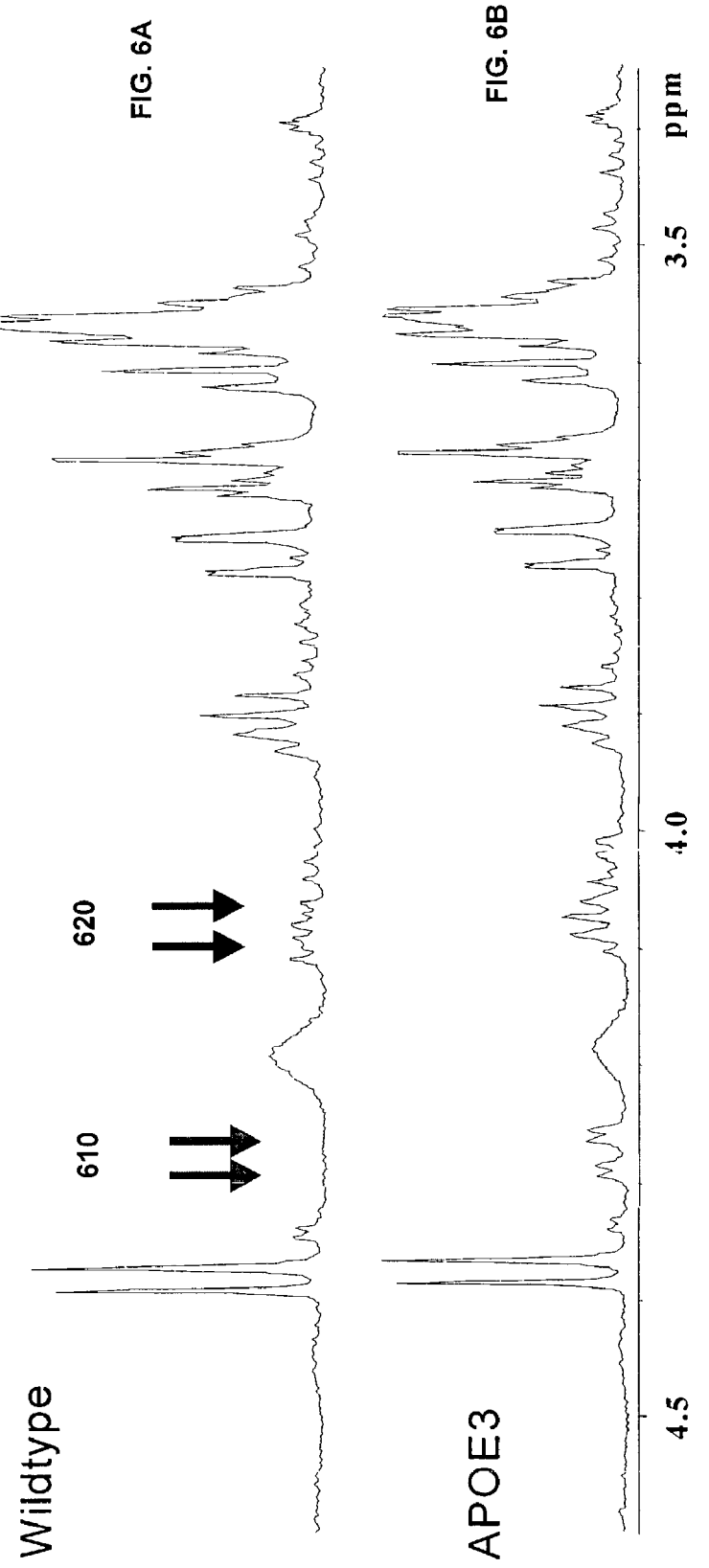

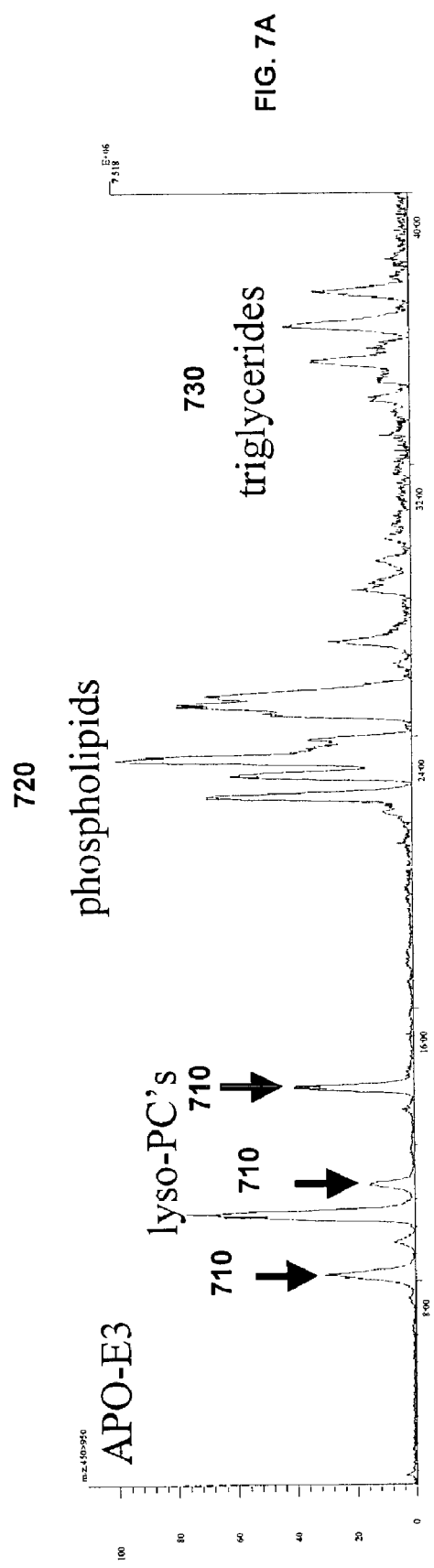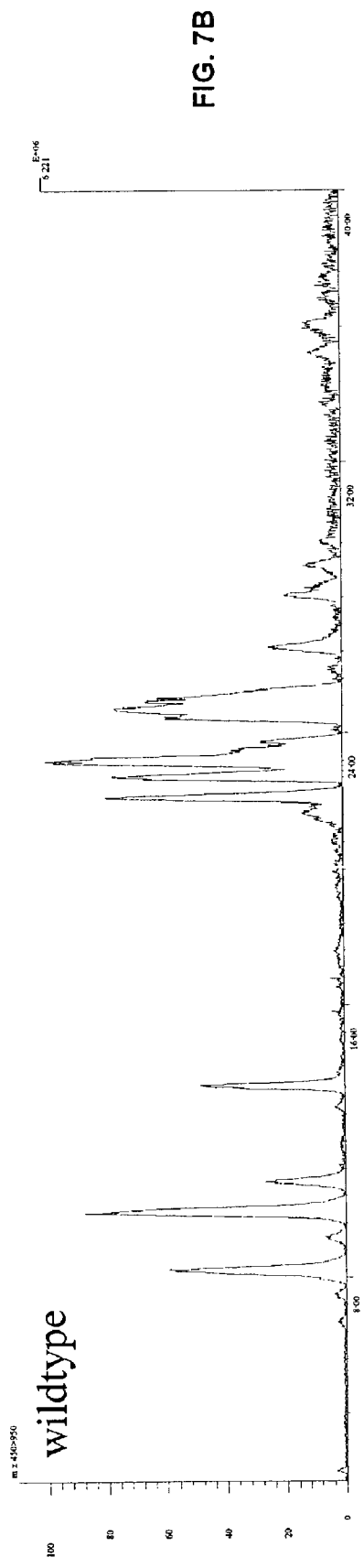
FIG. 7A
FIG. 7B

METHOD AND SYSTEM FOR PROFILING BIOLOGICAL SYSTEMS

CROSS REFERENCE TO RELATED APPLICATIONS

The present application claims the benefit of and priority to copending U.S. provisional application No. 60/312,145, filed Aug. 13, 2001, the entire disclosure of which is herein incorporated by reference.

FIELD OF THE INVENTION

The invention relates to the field of data processing and evaluation. In particular, the invention relates to an analytical technology platform for separating and measuring multiple components of a biological sample, and statistical data processing methods for identifying components and revealing patterns and relationships between and among the various measured components.

BACKGROUND

The characterization of complex mixtures has become important in a variety of research and application areas, including pharmaceuticals, biotechnological research, and nutraceutical (functional food) topics. One important area is the study of small molecules in pharmaceutical and biotechnology research, often referred to as metabolomics.

For example, an important challenge in the development of new drugs for complex (multi-factorial) diseases is the tracing and validation of biomarkers/surrogate markers. Moreover, it appears that instead of single biomarkers, biomarker-patterns may be necessary to characterize and diagnose homeostasis or disease states for such diseases.

In the discipline of metabolomics, the current art in the field of biological sample profiling is based either on measurement by nuclear magnetic resonance ("NMR") or by mass spectrometry ("MS") that focuses on a limited number of small molecule compounds. Both of these profiling approaches have limitations. The NMR approaches are limited in that they typically provide reliable profiles only of compounds present at high concentration. On the other hand, focused mass spectrometry based approaches do not require high concentrations but can provide profiles of only limited portions of the metabolome. What is needed is an approach that can address limitations in current profiling techniques and that facilitates the discernment of correlations between components or patterns of component (such as biomarker patterns).

SUMMARY OF THE INVENTION

The present invention addresses limitations in current profiling techniques by providing a method and system (or collectively "technology platform") utilizing hierarchical multivariate analysis of spectrometric data on one or more levels. The present invention further provides a technology platform that facilitates the discernment of similarities, differences, and/or correlations not only between single biomolecular components of a sample or biological system, but also between patterns of biomolecular components.

As used herein, the term "biomolecule component type" refers to a class of biomolecules generally associated with a level of a biological system. For example, gene transcripts are one example of a biomolecule component type that are generally associated with gene expression in a biological system, and the level of a biological system referred to as genomics or functional genomics. Proteins are another example of a biomolecule component type and generally associated with protein expression and modification, etc., and the level of a biological system referred to as proteomics. Further, another example of a biomolecule component type are metabolites, which are generally associated with the level of a biological system referred to as metabolomics.

The present invention provides a method and system for profiling a biological system utilizing a hierarchical multivariate analysis of spectrometric data to generate a profile of a state of a biological system. The states of a biological system that may be profiled by the invention include, but are not limited to, disease state, pharmacological agent response, toxicological state, biochemical regulation (e.g., apoptosis), age response, environmental response, and stress response. The present invention may use data on a biomolecule component type (e.g., metabolites, proteins, gene transcripts, etc.) from multiple biological sample types (e.g., body fluids, tissue, cells) obtained from multiple sources (such as, for example, blood, urine, cerebospinal fluid, epithelial cells, endothelial cells, different subjects, the same subject at different times, etc.). In addition, the present invention may use spectrometric data obtained on one or more platforms including, but not limited to, MS, NMR, liquid chromatography ("LC"), gas-chromatography ("GC"), high performance liquid chromatography ("HPLC"), capillary electrophoresis ("CE"), and any known form of hyphenated mass spectrometry in low or high resolution mode, such as LC-MS, GC-MS, CE-MS, LC-UV, MS-MS, $MS^n$, etc.

As used herein, the term "spectrometric data" includes data from any spectrometric or chromatographic technique and the term "spectrometric measurement" includes measurements made by any spectrometric or chromatographic technique. Spectrometric techniques include, but are not limited to, resonance spectroscopy, mass spectroscopy, and optical spectroscopy. Chromatographic techniques include, but are not limited to, liquid phase chromatography, gas phase chromatography, and electrophoresis.

As used herein, the terms "small molecule" and "metabolite" are used interchangeably. Small molecules and metabolites include, but are not limited to, lipids, steroids, amino acids, organic acids, bile acids, eicosanoids, peptides, trace elements, and pharmacophore and drug breakdown products.

In one aspect, the present invention provides a method of spectrometric data processing utilizing multiple steps of a multivariate analysis to process data in a hierarchal procedure. In one embodiment, the method uses a first multivariate analysis on a plurality of data sets to discern one or more sets of differences and/or similarities between them and then uses a second multivariate analysis to determine a correlation (and/or anti-correlation, i.e., negative correlation) between at least one of these sets of differences (or similarities) and one or more of the plurality of data sets. The method may further comprise developing a profile for a state of a biological system based on the correlation.

As used herein, the term "data sets" refers to the spectrometric data associated with one or more spectrometric measurements. For example, where the spectrometric technique is NMR, a data set may comprise one or more NMR spectra. Where the spectrometric technique is UV spectroscopy, a data set may comprise one or more UV emission or absorption spectra. Similarly, where the spectrometric technique is MS, a data set may comprise one or more mass spectra. Where the spectrometric technique is a chromatographic-MS technique (e.g., LC-MS, GC-MS, etc), a data set may comprise one or more mass chromatograms. Alternatively, a data set of a chromatographic-MS technique may comprise one or more a total ion current ("TIC") chromatograms or reconstructed TIC chromatograms. In addition, it should be realized that the term "data set" includes both raw spectrometric data and data that has been preprocessed (e.g., to remove noise, baseline, detect peaks, to normalize, etc.).

Moreover, as used, herein, the term "data sets" may refer to substantially all or a sub-set of the spectrometric data associated with one or more spectrometric measurements. For example, the data associated with the spectrometric measurements of different sample sources (e.g., experimental group samples v. control group samples) may be grouped into different data sets. As a result, a first data set may refer to experimental group sample measurements and a second data set may refer to control group sample measurements. In addition, data sets may refer to data grouped based on any other classification considered relevant. For example, data associated with the spectrometric measurements of a single sample source (e.g., experimental group) may be grouped into different data sets based, for example, on the instrument used to perform the measurement, the time a sample was taken, the appearance of the sample, etc. Accordingly, one data set (e.g., grouping of experimental group samples based on appearance) may comprise a sub-set of another data set (e.g., the experimental group data set).

In another aspect, the present invention provides a method of spectrometric data processing utilizing multivariate analysis to process data at two or more hierarchal levels of correlation. In one embodiment, the method uses a multivariate analysis on a plurality of data sets to discern correlations (and/or anti-correlations) between data sets at a first level of correlation, and then uses the multivariate analysis to discern correlations (and/or anti-correlations) between data sets at a second level of correlation. The method may further comprise developing a profile for a state of a biological system based on the correlations discerned at one or more levels of correlation.

In yet another aspect, the present invention provides a method of spectrometric data processing utilizing multiple steps of a multivariate analysis to process data sets in a hierarchal procedure, wherein one or more of the multivariate analysis steps further comprises processing data at two or more hierarchal levels of correlation. For example, in one embodiment, the method comprises: (1) using a first multivariate analysis on a plurality of data sets to discern one or more sets of differences and/or similarities between them; (2) using a second multivariate analysis to determine a first level of correlation (and/or anti-correlation) between a first sets of differences (or similarities) and one or more of the data sets; and (3) using the second multivariate analysis to determine a second level of correlation (and/or anti-correlation) between the first sets of differences (or similarities) and one or more of the data sets. The method of this aspect may also comprise developing a profile for a state of a biological system based on the correlations discerned at one or more levels of correlation.

In other aspects of the invention, the present invention provides systems adapted to practice the methods of the invention set forth above. In one embodiment, the system comprises a spectrometric instrument and a data processing device. In another embodiment, the system further comprises a database accessible by the data processing device. The data processing device may comprise an analog and/or digital circuit adapted to implement the functionality of one or more of the methods of the present invention.

In some embodiments, the data processing device may implement the functionality of the methods of the present invention as software on a general purpose computer. In addition, such a program may set aside portions of a computer's random access memory to provide control logic that affects the hierarchical multivariate analysis, data preprocessing and the operations with and on the measured interference signals. In such an embodiment, the program may be written in any one of a number of high-level languages, such as FORTRAN, PASCAL, C, C++, or BASIC. Further, the program may be written in a script, macro, or functionality embedded in commercially available software, such as EXCEL or VISUAL BASIC. Additionally, the software could be implemented in an assembly language directed to a microprocessor resident on a computer. For example, the software could be implemented in Intel 80×86 assembly language if it were configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

In a further aspect, the present invention provides an article of manufacture where the functionality of a method of the present invention is embedded on a computer-readable medium, such as, but not limited to, a floppy disk, a hard disk, an optical disk, a magnetic tape, a PROM, an EPROM, CD-ROM, or DVD-ROM.

BRIEF DESCRIPTION OF THE DRAWINGS

The foregoing and other features and advantages of the invention, as well as the invention itself, will be more fully understood from the description, drawings, and claims that follow. The drawings are not necessarily drawn to scale, and like reference numerals refer to the same parts throughout the different views.

FIGS. 3A and 3B are examples of partial 400 MHz $^1$H-NMR spectra for urine samples of wildtype mouse samples, FIG. 3A and APO E3 mouse samples, FIG. 3B.

FIGS. 4A and 4B are examples of partial 400 MHz $^1$H-NMR spectra for urine samples of wildtype mouse samples, FIG. 4A and APO E3 mouse samples, FIG. 4B.

FIGS. 5A and 5B are examples of partial 400 MHz $^1$H-NMR spectra for blood plasma samples of wildtype mouse samples, FIG. 5A, and APO E3 mouse samples, FIG. 5B.

FIGS. 6A and 6B are examples of partial 400 MHz $^1$H-NMR spectra for blood plasma samples of wildtype mouse samples, FIG. 6A, and APO E3 mouse samples, FIG. 6B.

FIGS. 7A and 7B are examples of a blood plasma lipid profile obtained by a LC-MS spectrometric technique using ESI on APO E3 mouse blood plasma samples, FIG. 7A, and wildtype mouse samples, FIG. 7B.

DETAILED DESCRIPTION

Figure 1A:
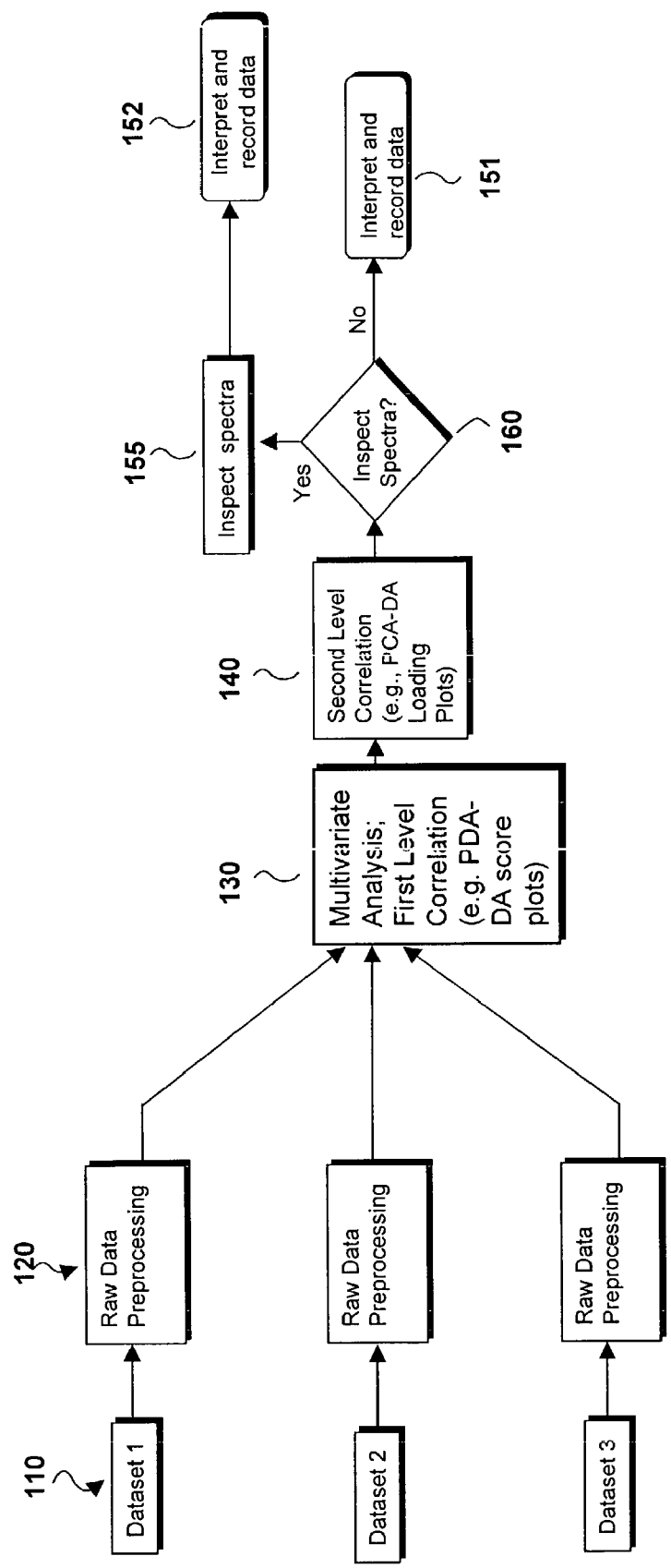
FIG. 1A is a flow diagram of analyzing a plurality of data sets according to various embodiments of the present invention.

Referring to FIG. 1A, a flow chart of one embodiment of a method according to the present invention is shown. One or more of a plurality of data sets 110 are preferably subjected to a preprocessing step 120 prior to multivariate analysis. Suitable forms of preprocessing include, but are not limited to, data smoothing, noise reduction, baseline correction, normalization and peak detection. Preferable forms of data preprocessing include entropy-based peak detection (such as disclosed in pending U.S. patent application, Ser. No. 09/920,993, filed Aug. 2, 2001, the entire contents of which are hereby incorporated by reference) and partial linear fit techniques (such as found in J. T. W. E. Vogels et al., "Partial Linear Fit: A New NMR Spectroscopy Processing Tool for Pattern Recognition Applications," Journal of Chemometrics, vol. 10, pp. 425-38 (1996)). A multivariate analysis is then performed at a first level of correlation 130 to discern differences (and/or similarities) between the data sets. Suitable forms of multivariate analysis include, for example, principal component analysis ("PCA"), discriminant analysis ("DA"), PCA-DA, canonical correlation ("CC"), partial least squares ("PLS"), predictive linear discriminant analysis ("PLDA"), neural networks, and pattern recognition techniques. In one embodiment, PCA-DA is performed at a first level of correlation that produces a score plot (i.e., a plot of the data in terms of two principal components; see, e.g, FIGS. 8-12 which are described further below). Subsequently, the same or a different multivariate analysis is performed on the data sets at a second level of correlation 140 based on the differences (and/or similarities) discerned from the first level of correlation.

For example, in one embodiment, where the first level comprises a PCA-DA score plot, the second level of correlation comprises a loading plot produced by a PCA-DA analysis. This second level of correlation bears a hierarchical relationship to the first level in that loading plots provide information on the contributions of individual input vectors to the PCA-DA that in turn are used to produce a score plot. For example, where each data set comprises a plurality of mass chromatograms, a point on a score plot represents mass chromatograms originating from one sample source. In comparison, a point on a loading plot represents the contribution of a particular mass (or range of masses) to the correlations between data sets. Similarly, where each data set comprises a plurality of NMR spectra, a point on a score plot represents one NMR spectrum. In comparison, a point on the corresponding loading plot represents the contribution of a particular NMR chemical shift value (or range of values) to the correlations between data sets.

Referring again to FIG. 1A, based on the correlations discerned in the analysis at the first level of correlation 130 and/or that at the second level of correlation 140 a profile may be developed 151 ("NO" to inspect spectra query 160). For example, the region in a score plot where the data points fall for a certain group of data sets may comprise a profile for the state of a biological system associated with that group. Further, the profile may comprise both the above region in a score plot and a specific level of contribution from one or more points in an associated loading plot. For example, where the data sets comprise mass chromatograms and/or mass spectra, a biological system may only fit into the profile of a state if spectrometric data sets from appropriate samples fall in a certain region of the score plot and if the mass chromatograms for a particular range of masses provide a significant contribution to the correlation observed in the score plot. Similarly, where the data sets comprise NMR spectra, a biological system may only fit into the profile of a state if spectrometric data sets from appropriate samples fall in a certain region of the score plot and if a particular range of chemical shift values in the NMR spectra provide a significant contribution to the correlation observed in the score plot.

In addition, the method may further include a step of inspection 155 of one or more specific spectra of the data sets ("YES" to inspect spectra query 160) based on the correlations discerned in the analysis at the first level of correlation 130 and/or that at the second level of correlation 140. A profile based on this inspection is then developed 152. For example, where the spectra of the data sets comprise mass chromatograms, the method inspects the mass chromatograms of those mass ranges showing a significant contribution to the correlation based on the loading plot. Inspection of these mass chromatograms, for example, may reveal what species of chemical compounds are associated with the profile. Such information may be of particular importance for biomarker identification and drug target identification.

Figure 1B:
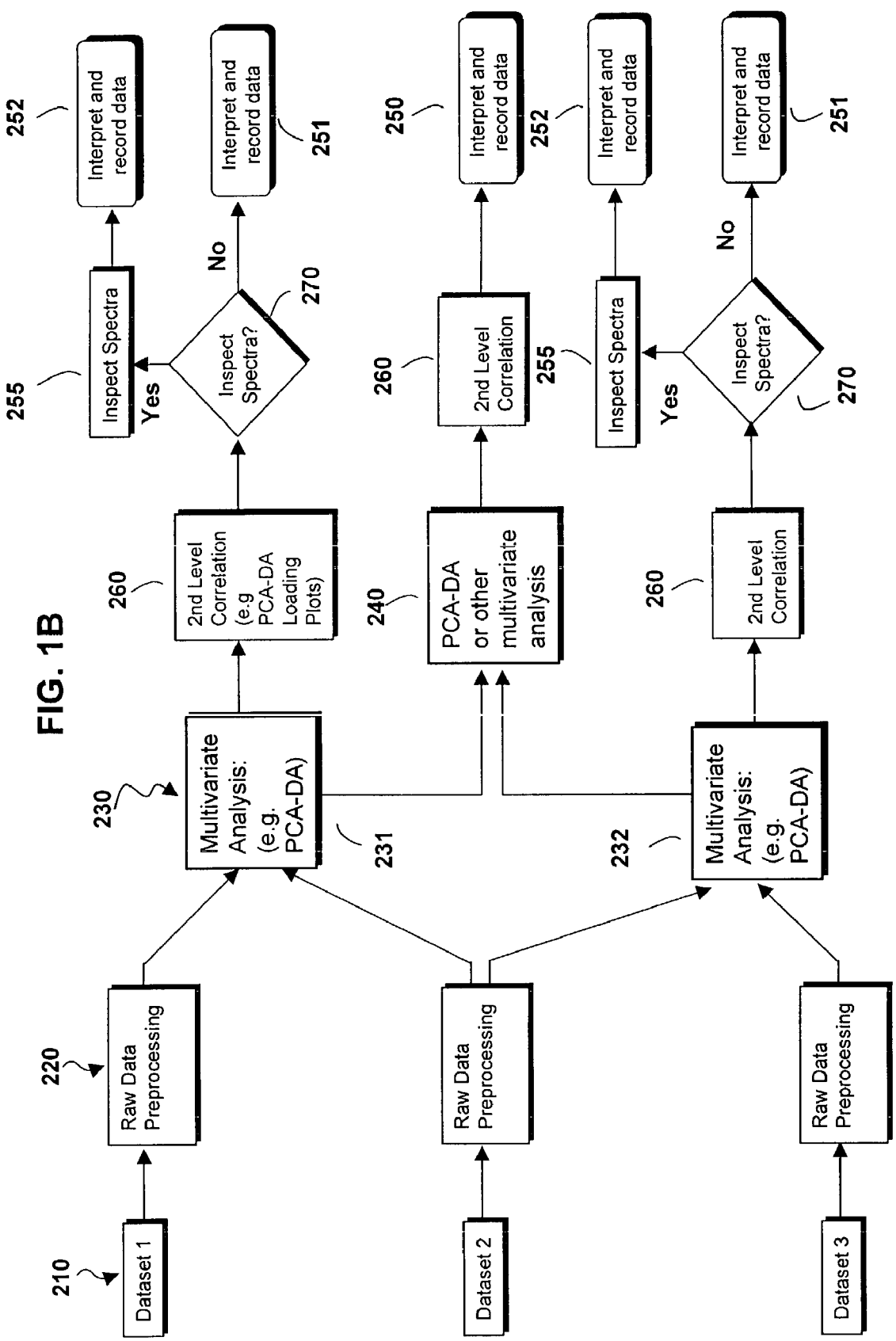
FIG. 1B is a flow diagram of analyzing a plurality of data sets according to various other embodiments of the present invention.

Referring to FIG. 1B, a flow chart of another embodiment of a method according to the present invention is shown. One or more of a plurality of data sets 210 are preferably subjected to a preprocessing step 220 prior to multivariate analysis. A first multivariate analysis is then performed 230 on a plurality of data sets to discern one or more sets of differences and/or similarities between them. The first multivariate analysis may be performed between sub-sets of the data sets. For example, the first multivariate analysis may be performed between data set 1 and data set 2, 231 and the first multivariate analysis may be performed separately between data set 2 and data set 3, 232. The method then uses a second multivariate analysis 240 to determine a correlation between at least one of the sets of differences (or similarities) discerned in the first multivariate analysis and one or more of the data sets. This second multivariate analysis 240 bears a hierarchal relationship to the first 230 in that the differences between data sets are discerned in a hierarchal fashion. For example, the differences between data sets 1 and 2 (and data sets 2 and 3) are first discerned 231, 232 and then those differences are subjected to further multivariate analysis 240. In one embodiment, a profile based on the correlations discerned in the second multivariate analysis 240 is developed 250.

In addition, any of the multivariate analysis steps 231, 232, 240 may further comprise a step of performing the same or a different multivariate analysis at another level of correlation 260 (for example, such as described with respect to FIG. 1A) based on the differences (and/or similarities) discerned from the level of correlation used in a prior multivariate analysis step 231, 232, 240. A profile based on the information from one or more of these levels of correlation may then be developed 250, 251 ("NO" to inspect spectra query 270). Alternatively, the method may further include a step of inspection 255 of one or more specific spectra of the data sets ("YES" to inspect spectra query 270) based on the correlations discerned in the analysis at one ore more levels of correlation and/or one or more multivariate analysis steps. A profile based on this inspection then may be developed 252.

The methods of the present invention may be used to develop profiles on any biomolecular component type. Such profiles facilitate the development of comprehensive profiles of different levels of a biological system, such as, for example, genome profiles, transcriptomic profiles, proteome profiles, and metaboiome profiles. Further, such methods may be used for data analysis of spectrometric measurements (of, for example, plasma samples from a control and patient group), may be used to evaluate any differences in single components or patterns of components between the two groups exist in order to obtain a better insight into underlying biological mechanisms, to detect novel biomarkers/surrogate markers, and/or develop intervention routes.

In various embodiments, the present invention provides methods for developing profiles of metabolites and small molecules. Such profiles facilitate the development of comprehensive metabolome profiles. In other various embodiments, the present invention provides methods for developing profiles of proteins, protein-complexes and the like. Such profiles facilitate the development of comprehensive proteome profiles. In yet other various embodiments, the present invention provides methods for developing profiles of gene transcripts, mRNA and the like. Such profiles facilitate the development of comprehensive genome profiles.

In one version of these embodiments, the method is generally based on the following steps: (1) selection of biological samples, for example body fluids (plasma, urine, cerebral spinal fluid, saliva, synovial fluid etc.); (2) sample preparation based on the biochemical components to be investigated and the spectrometric techniques to be employed (e.g., investigation of lipids, proteins, trace elements, gene expression, etc.); (3) measurement of the high concentration components in the biological samples using methods mass spectrometry and NMR; (4) measurement of selected molecule subclasses using NMR-profiles and preferred MS-approaches to study compounds such as, for example, lipids, steroids, bile acids, eicosanoids, (neuro)peptides, vitamins, organic acids, neurotransmitters, amino acids, carbohydrates, ionic organics, nucleotides, inorganics, xenobiotics etc.; (5) raw data preprocessing; (6) data analysis using multivariate analysis according to any of the methods of the present invention (e.g., to identify patterns in measurements of single subclasses of molecules or in measurements of high concentration components using NMR or mass spectrometry); and (7) using of multivariate analysis to combine data sets from distinct experiments and find patterns of interest in the data. In addition, the method may further comprise a step of (8) acquiring data sets at a number of points in time to facilitate the monitoring of temporal changes in the multivariate patterns of interest.

The methods of the present invention may be used to develop profiles on a biomolecular component type obtained from a wide variety of biological sample types including, but not limited to, blood, blood plasma, blood serum, cerebrospinal fluid, bile acid, saliva, synovial fluid, pluearl fluid, pericardial fluid, peritoneal fluid, feces, nasal fluid, ocular fluid, intracellular fluid, intercellular fluid, lymph urine, tissue, liver cells, epithelial cells, endothelial cells, kidney cells, prostate cells, blood cells, lung cells, brain cells, adipose cells, tumor cells and mammary cells.

In another aspect, the present invention provides an article of manufacture where the functionality of a method of the present invention is embedded on a computer-readable medium, such as, but not limited to, a floppy disk, a hard disk, an optical disk, a magnetic tape, a PROM, an EPROM, CD-ROM, or DVD-ROM. The functionality of the method may be embedded on the computer-readable medium in any number of computer-readable instructions, or languages such as, for example, FORTRAN, PASCAL, C, C++, BASIC and assembly language. Further, the computer-readable instructions can, for example, be written in a script, macro, or functionally embedded in commercially available software (such as, e.g., EXCEL or VISUAL BASIC).

Figure 19:
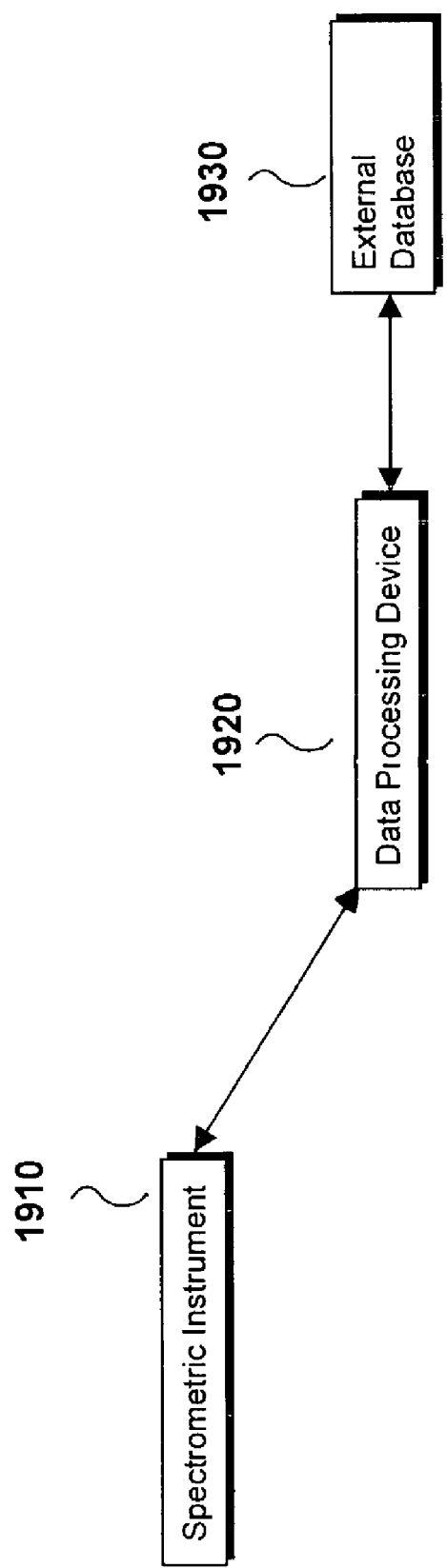
FIG. 19 is a schematic representation of one embodiment of a system adapted to practice the methods of the invention.

In other aspects, the present invention provides systems adapted to practice the methods of the present invention. Referring to FIG. 19, in one embodiment, the system comprises one or more spectrometric instruments 1910 and a data processing device 1920 in electrical communication, wireless communication, or both. The spectrometric instrument may comprise any instrument capable of generating spectrometric measurements useful in practicing the methods of the present invention. Suitable spectrometric instruments include, but are not limited to, mass spectrometers, liquid phase chromatographers, gas phase chromatographer, and electrophoresis instruments, and combinations thereof. In another embodiment, the system further comprises an external database 1930 storing data accessible by the data processing device, wherein the data processing device implement the functionality of one or more of the methods of the present invention using at least in part data stored in the external database.

The data processing device may comprise an analog and/or digital circuit adapted to implement the functionality of one or more of the methods of the present invention using at least in part information provided by the spectrometric instrument. In some embodiments, the data processing device may implement the functionality of the methods of the present invention as software on a general purpose computer. In addition, such a program may set aside portions of a computer's random access memory to provide control logic that affects the spectrometric measurement acquisition, multivariate analysis of data sets, and/or profile development for a biological system. In such an embodiment, the program may be written in any one of a number of high-level languages, such as FORTRAN, PASCAL, C, C++, or BASIC. Further, the program can be written in a script, macro, or functionality embedded in proprietary software or commercially available software, such as EXCEL or VISUAL BASIC. Additionally, the software could be implemented in an assembly language directed to a microprocessor resident on a computer. For example, the software can be implemented in Intel 80×86 assembly language if it is configured to run on an IBM PC or PC clone. The software may be embedded on an article of manufacture including, but not limited to, a computer-readable program medium such as a floppy disk, a hard disk, an optical disk, a magnetic tape, a PROM, an EPROM, or CD-ROM.

EXAMPLE

Small Molecule Study of the APO E3 Mouse Model for Atherosclerosis

An example of the practice of various embodiments of the present invention is illustrated below in the context of a small molecule study of the APO E3 Leiden transgenic mouse model.

A. The APO E3 Leiden Mouse

The APO E3 Leiden mouse model is a transgenic animal model described in "The Use of Transgenic Mice in Drug Discovery and Drug Development," by P. L. B. Bruijnzeel, TNO Pharma, Oct. 24, 2000. Briefly, the APO E3-Leiden allele is identical to the APO E4 (Cys112→Arg) allele, but includes an in frame repeat of 21 nucleotides in exon 4, resulting in tandem repeat of codon 120-126 or 121-127. Transgenic mice expressing APO E3-Leiden mutation are known to have hyperlipidemic phenotypes that under specific conditions lead to the development of atherosclerotic plaques. The model has a high predicted success rate in finding differences at the small molecule (metabolite) and protein levels, while the gene level is very well characterized.

In the present example, 10 wildtype and 10 APO E3 male mice were sacrificed after collection of urine in metabolic cages. The APO E3 mice were created by insertion of a well-defined human gene cluster (APO E3-APC1), and a very homogeneous population was generated by at least 20 inbred generations.

The following samples were available for analysis: (1) 10 wildtype and 10 APO E3 urine samples (about 0.5 ml/animal or more); (2) 10 wildtype and 10 APO E3 (heparin) plasma samples (about 350 μl/animal); (3) 10 wildtype and 10 APO E3 liver samples. From the plasma samples 100 microliters were used for NMR and the same samples were used for LC-MS, about 250 μl is available for protein work and duplicates. All samples were stored at −20 C. In total, 19 plasma samples were received. One sample, animal #6 (APO-E3 Leiden group) was not present. After cleanup, (described below) the portions reserved for proteomics research were transferred to −70° C.

B. Experimental Details, Plasma and Urine Samples

Plasma sample extraction was accomplished with isopropanol (protein precipitation). LC-MS lipid profile measurements of the plasma samples were obtained with on an electrospray ionization ("ESI") and atmospheric pressure chemical ionization ("APCI") LC-MS system. The resultant raw data was preprocessed with an entropy-based peak detection technique substantially similar to that disclosed in pending U.S. patent application Ser. No. 09/920,993, filed Aug. 2, 2001. The preprocessed data was then subjected to principal component analysis ("PCA") and/or discriminant analysis ("DA") according to the methods of the present invention. The raw data from the NMR measurements of the plasma samples was subjected to a pattern recognition analysis ("PARC"), which included preprocessing (such as a partial linear fit), peak detection and multivariate statistical analysis.

Urine samples were prepared and NMR measurements of the urine samples were obtained. The raw NMR data on the urine samples was also subjected to a PARC analysis, which included preprocessing, peak detection and multivariate statistical analysis.

B.1. Mouse Blood Plasma Preparation and Cleanup

The mouse plasma samples were thawed at room temperature. Aliquots of 100 μl were transferred to a clean eppendorf vials and stored at −70° C. The sample volume for sample #12 was low and only 50 μl was transferred. For NMR and LC-MS lipid analysis 150 μl aliquots were transferred to clean eppendorf vials.

Plasma samples were cleaned up and handled substantially according to the following protocol: (1) add 0.6 ml of isopropanol; (2) vortex; (3) centrifuge at 10,000 rpm for 5 min.; (4) transfer 500 μl to clean tube for NMR analysis; (5) transfer 100 μl to clean eppendorf vial; (6) add 400 μl water and mix; and (7) transfer 200 μl to autosampler vial insert. The remaining extract and pellet (precipitated protein) were stored at −20° C.

B.2. Human Blood Plasma Preparation and Cleanup

Human heparin plasma was obtained from a blood bank. In a glass tube, 1 ml of human plasma and 4 ml of isopropanol were mixed (vortexed). After centrifugation, 1 ml of extract was transferred to a tube and 4 ml of water was added. The resulting solution was transferred to 4 autosampler vials (1 ml).

B.3. LC-MS of Blood Plasma Samples:

Spectrometric measurements of plasma samples were made with a combination HPLC-time-of-flight MS instrument. Effluent emerging from the chromatograph was ionized by electrosrpay ionization ("ESI") and atmospheric pressure chemical ionization ("APCI"). Typical instrument parameters used with HPLC instrument are given in Table 1 and details of the gradient in Table 2; typical parameters for the ESI source are given in Table 3, and those for the APCI source are given in Table 4.

TABLE 1

HPLC Parameters

| | |
|---|---|
| Column: | Inertsil ODS3 5 μm, 100 × 3 mm i.d. (Chrompack); R$_2$ guard column (Chrompack) |
| Mobile phase A: | 5% acetonitrile, 50 μl MeCN, water ad 1000 ml, 10 ml ammonium acetate solution (1 mol/l), 1 ml formic acid |
| Mobile phase B: | 30% isopropanol in acetonitrile, 300 ml isopropanol, acetonitrile ad 1000 ml, 10 ml ammonium acetate solution (1 mol/l), 1 ml formic acid |
| Mobile phase C: | 50% dichloromethane in isopropanol, 500 ml isopropanol, dichloromethane ad 1000 ml, 10 ml ammonium acetate solution (1 mol/l), 1 ml formic acid |
| Temperature: | ca. 20° C. (conditioned laboratory) |
| Injection volume: | 75 μl |

TABLE 2

HPLC Gradient

| Time (min) | Flow (ml/min) | % A | % B | % C |
|---|---|---|---|---|
| 0 | 0.7 | 70 | 30 | |
| 2 | 0.7 | 70 | 30 | |
| 15 | 0.7 | 5 | 95 | |
| 35 | 0.7 | 5 | 35 | 60 |
| 40 | 0.7 | 5 | 35 | 60 |
| 41 | 0.7 | 5 | 95 | |
| 45 | 0.7 | 70 | 30 | |

TABLE 3

Electrospray (ESI) Parameters

| | |
|---|---|
| Mode: | positive (+) |
| Cap. Heater: | 250° C. |
| Spray voltage: | 4 kV |
| Sheath gas: | 70 units |
| Aux. Gas: | 15 units |
| Scan: | 200 to 1750, 1 s/scan |

TABLE 4

| Atmospheric Pressure Chemical Ionization (APCI) Parameters | |
|---|---|
| Mode: | positive (+) |
| Cap. Heater: | 175° C. |
| Vaporizer: | 450° C. |
| Corona: | 5 µA |
| Sheath gas: | 70 units |
| Aux. Gas: | 0 units |
| Scan: | 200 to 1750, 1 s/scan |

The injection sequence for samples was as follows. The mouse plasma extracts were injected twice in a random order. The human plasma extract was injected twice at the start of the sequence and after every 5 injections of the mouse plasma extracts to monitor the stability of the LC-MS conditions. The random sequence was applied to prevent the detrimental effects of possible drift on the multivariate statistics.

B.4. NMR of Plasma and Urine Samples:

NMR spectrometric measurements of plasma samples were made with a 400 MHz $^1$H-NMR. Samples for the NMR were prepared and handled substantially in accord with the following protocol. Isopropanol plasma extracts (500 µl from 2.3.1) were dried under nitrogen, whereafter the residues were dissolved in deuterated methanol (MeOD). Deuterated methanol was selected because it gave the best NMR spectra when chloroform, water, methanol and dimethylsulfoxide (all deuterated) were compared.

NMR spectrometric measurements of urine samples were also made with a 400 MHz $^1$H-NMR.

C. Spectrometric Measurements and Analysis

The following spectrometric measurements were made at metabolite/small molecule level:

NMR-measurements of urine, multiple measurements (preferably triplicate measurements) on a total of 40 samples;

NMR-measurement of plasma, multiple measurements (preferably triplicate measurements) on a total of 40 samples; and LC/MS-measurement of plasma (plasmalipid profile), multiple measurements (preferably triplicate measurements) on a total of 40 samples.

Figure 2A:
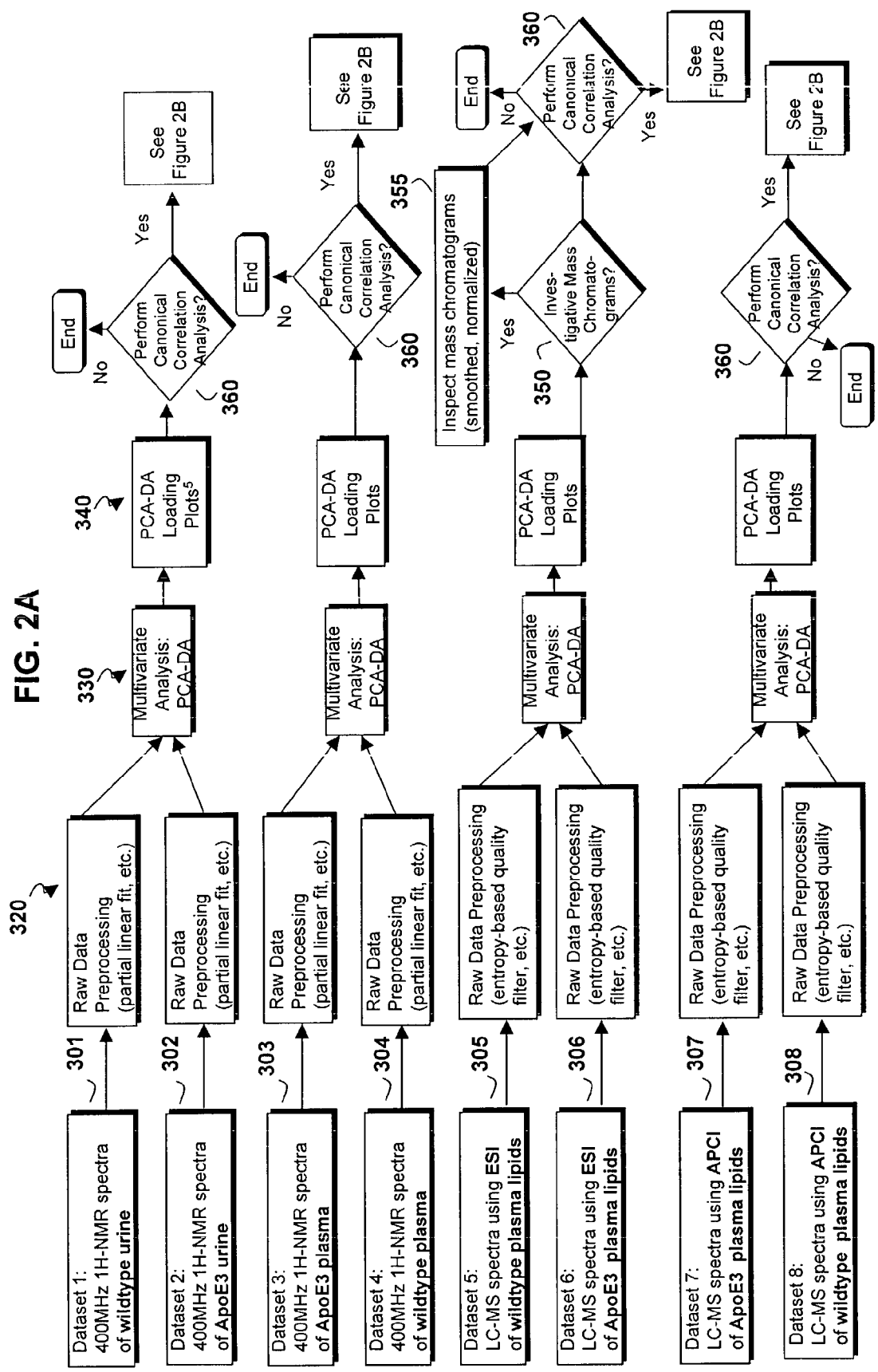
FIGS. 2A and 2B are flow diagrams of the analysis performed according to various embodiments of the present invention on a plurality of data sets of multiple biological sample types obtained from wildtype mice and APO E3 Leiden mice.
Figure 2B:
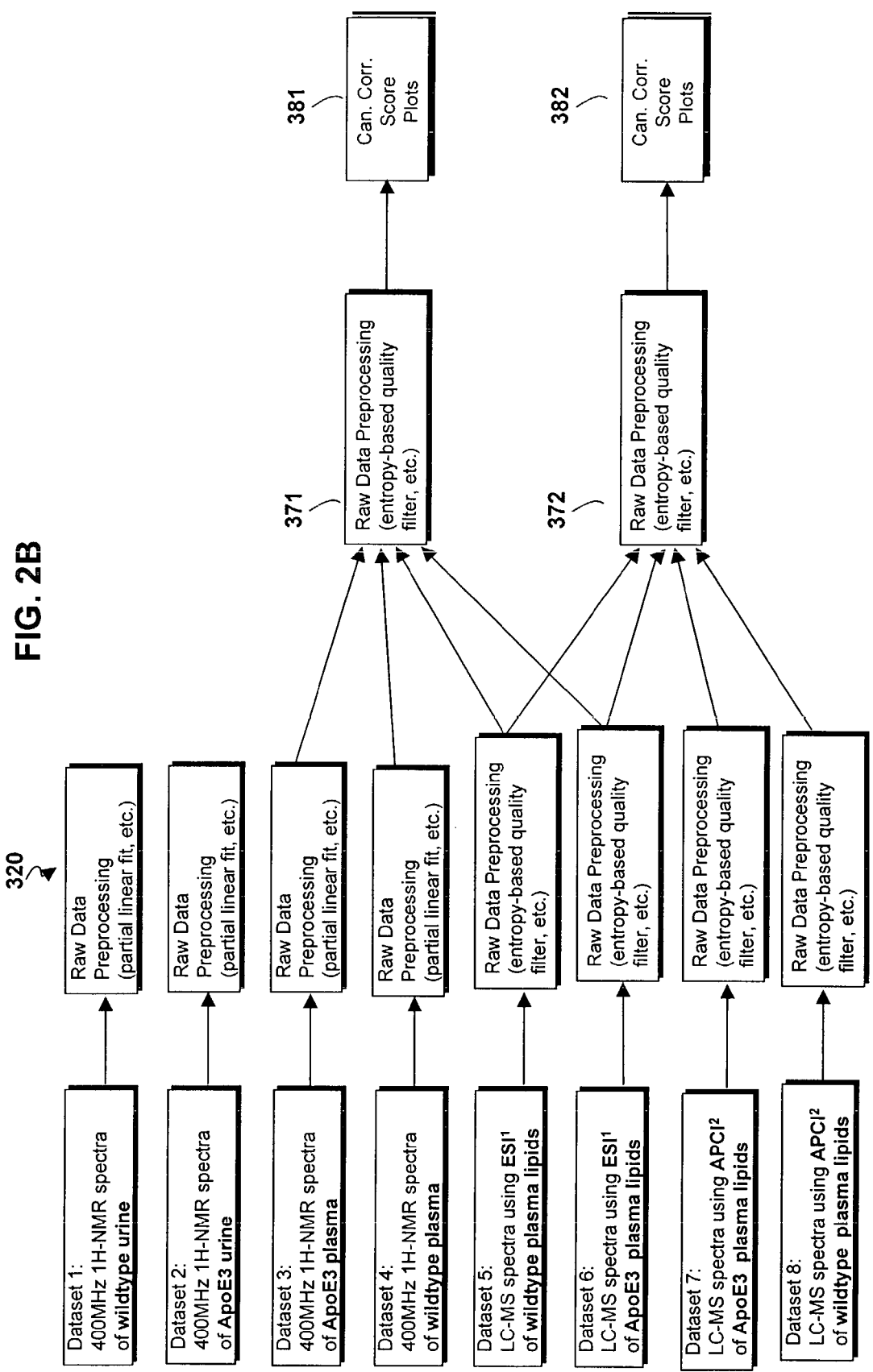

A flow chart illustrating the analysis of the spectrometric data of this example according to one embodiment of the present invention is shown in FIGS. 2A and 2B.

Referring to FIG. 2A, the spectrometric data obtained was grouped into eight data sets 301-308. The data sets were as follows: (1) data set 1 comprised 400 MHz 1H-NMR spectra of wildtype mouse urine samples 301; (2) data set 2 comprised 400 MHz 1H-NMR spectra of APO E3 mouse urine samples 302; (3) data set 3 comprised 400 MHz 1H-NMR spectra of APO E3 mouse blood plasma samples 303; (4) data set 4 comprised 400 MHz 1H-NMR spectra of wildtype mouse blood plasma samples 304; (5) data set 5 comprised LC-MS spectra (using ESI) of wildtype mouse blood plasma lipid samples 305; (6) data set 6 comprised LC-MS spectra (using ESI) of APO E3 mouse blood plasma lipid samples 306; (7) data set 7 comprised LC-MS spectra (using APCI) of APO E3 mouse blood plasma lipid samples 307; and (8) data set 8 comprised LC-MS spectra (using APCI) of wildtype mouse blood plasma lipid samples 308. Examples of the spectrometric measurements obtained for each of these data sets is as follows: FIGS. 3A and 4A for data set 1; FIGS. 3B and 4B for data set 2; FIGS. 5B and 6B for data set 3; FIGS. 5A and 6A for data set 4; FIG. 7B for data set 5; and FIG. 7A for data set 6. Various features were noted in the data of FIGS. 3A-7B.

Referring to FIGS. 3A and 3B, it was noted that peaks associated with hippuric acid 410 were observed in the wildtype mouse urine sample $^1$H-NMR spectra, while such peaks were substantially absent from the APO E3 mouse urine sample $^1$H-NMR spectra, indicating a possible biochemical process unique to the APO E3 mouse. Referring to FIGS. 4A and 4B, in addition, peaks associated with an unidentified component 420 were observed in the wildtype mouse urine sample $^1$H-NMR spectra, which were also substantially absent from corresponding $^1$H-NMR spectra of the APO E3 mouse urine samples.

Referring to FIGS. 5A and 5B, a two series of peaks 510, 520 were observed in the APO E3 mouse blood plasma sample $^1$H-NMR spectra, which were either substantially absent from the wildtype spectra 510 or substantially reduced 520. As shown in FIGS. 6A and 6B, the peaks associated with the first series of peaks 510 are substantially absent from the resonance shift region in wildtype spectra 610, whole the second series of peaks 520 are present but reduced in the wildtype spectra 620.

Referring to FIGS. 7A and 7B, it was noted that peaks associated with lyso-phosphatidylcholines ("lyso-PC") 710 were slightly reduced in intensity in the APO E3 mouse spectra relative to those for the wildtype, that peaks associated with phospholipids 720 were substantially equal in intensity between the APO E3 and wildtype spectra, and that peaks associated with triglycerides 730 were substantially increased in intensity in the APO E3 mouse spectra relative to those for the wildtype.

The raw data from data sets 1 to 8 was preprocessed 320 and a first multivariate analysis was performed between data sets 1 and 2, 3 and 4, 5 and 6, and 7 and 8, respectively, each at a first level of correlation 330, i.e., PCA-DA score plots. Examples of the results of the first multivariate analysis at a first level of correlation are illustrated in FIGS. 8-11 for data sets 1 and 2; FIG. 12 for data sets 3 and 4; and FIG. 13 for data sets 5 and 6 (which includes data from human samples). Data from the first multivariate analysis was then used to produce an analysis at a second level of correlation 340, i.e., PCA-DA loading plots. An example of one such PCA-DA loading plot is shown in FIG. 14.

Figure 8:
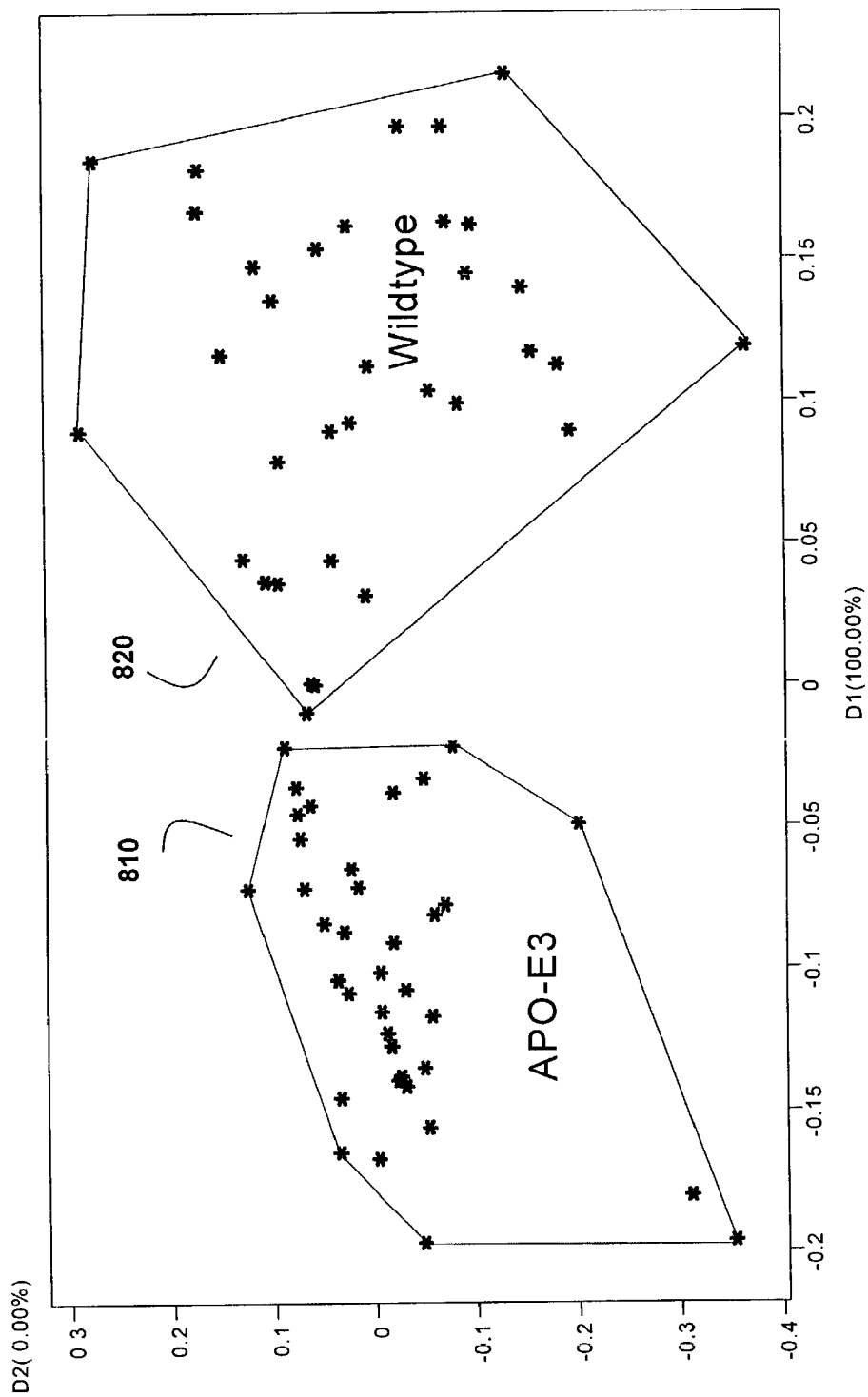
FIG. 8 is an example of a PCA-DA score plot of the NMR data for the urine samples of data sets 1 and 2 of FIGS. 2A and 2B.

Referring to FIG. 8, a PCA-DA score plot of the NMR data for the urine samples of data sets 1 and 2 is shown. As illustrated, the analysis groups NMR data for APO E3 and wildtype group into two substantially distinct regions in the score plot, an APO E3 region 810 and a wildtype region 820, indicating that urine samples alone may suffice to develop a profile that reflects the transgenic nature of the APO E3 mice and serve as a bodyfluid biomarker profile for distinguishing APO E3 mice from other types of mice.

Figure 9:
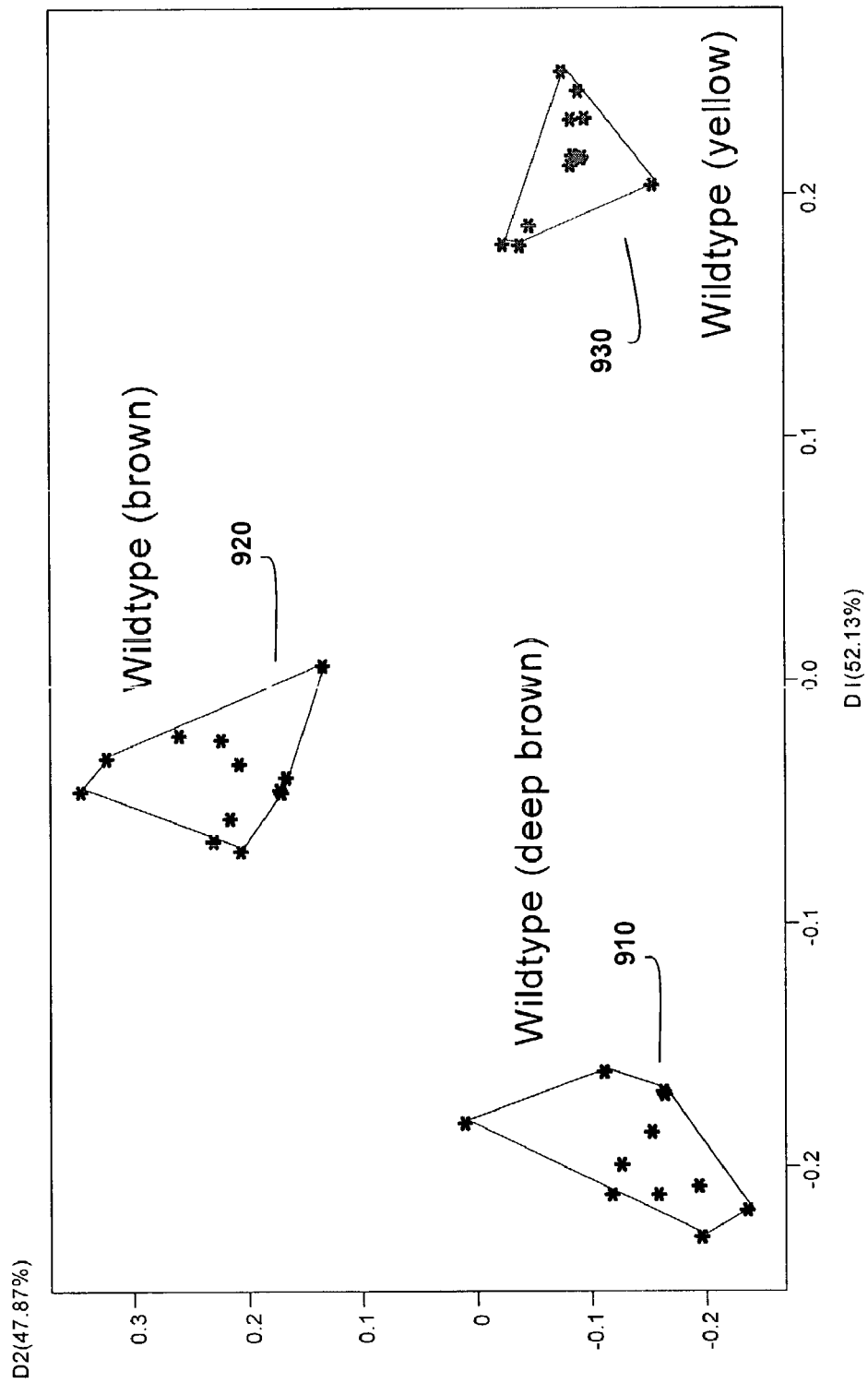
FIG. 9 is an example of a PCA-DA score plot of the NMR data for the urine samples of data set 1 (wildtype mouse) of FIGS. 2A and 2B.

Referring to FIG. 9, a score plot of the NMR data for the urine samples of data set 1 is shown. As illustrated, the analysis indicates that there are similarities and differences within the urine samples of data set 1 that correlate with urine color. Specifically, the analysis illustrates three distinct regions in the score plot correlated to deep brown urine 910, brown urine 920, and yellow urine 930. FIG. 9 illustrates that there are three distinct subgroups of mouse urine profiles in the wildtype mouse cohort.

Figure 10:
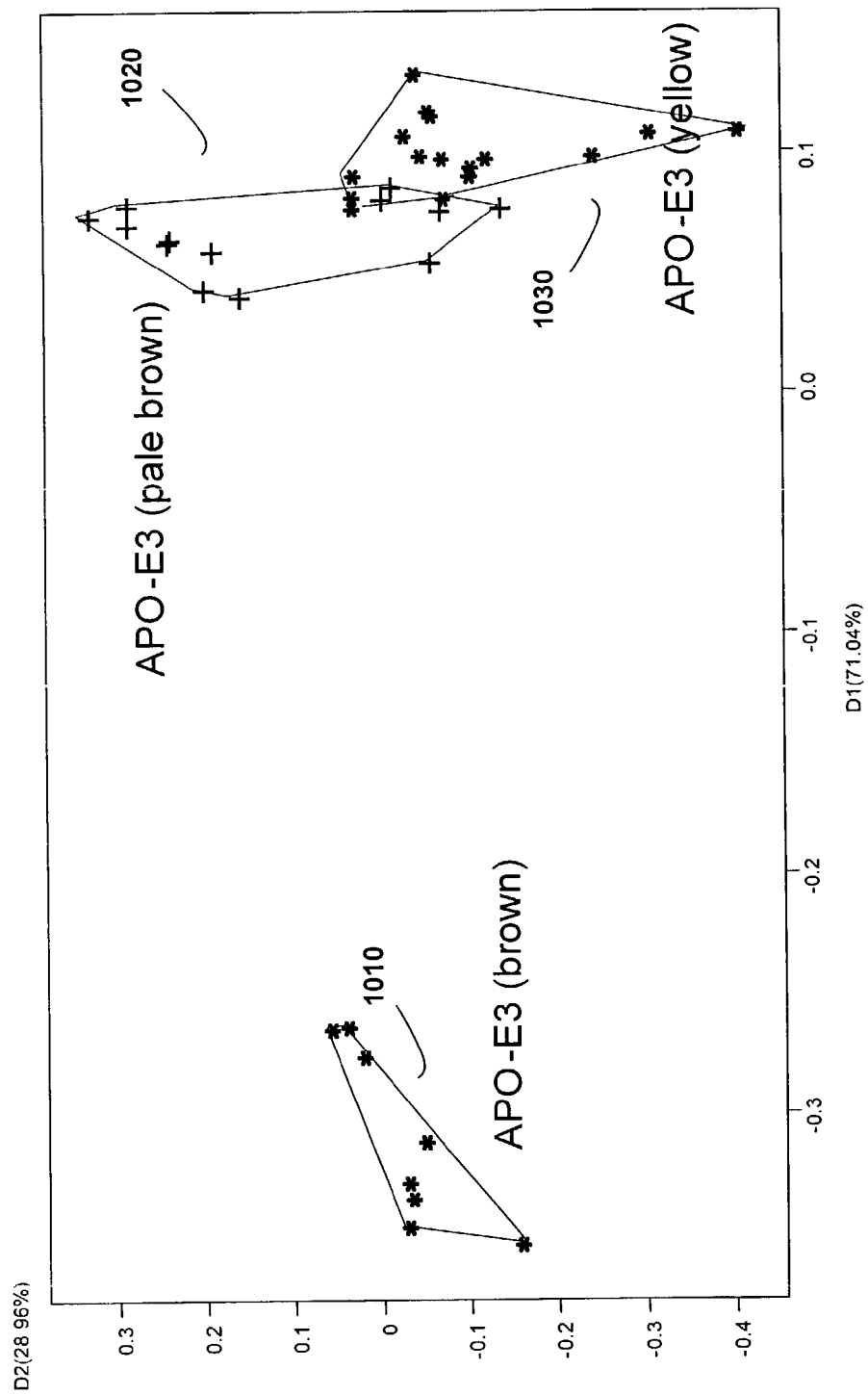
FIG. 10 is an example of a PCA DA score plot of the NMR data for the urine samples of data set 2 (APO E3 mouse) of FIGS. 2A and 2B.

Similarly in FIG. 10, a score plot of the NMR data for the urine samples of data set 2 is shown. As illustrated, the analysis indicates that there are similarities and differences within the urine samples of data set 2 that correlates with urine color. Specifically, the analysis illustrates three regions in the score plot, one correlated to brown urine 1010, and another to pale brown urine 1020, that slightly overlaps with a yellow urine correlated region 1030. FIG. 10 illustrates that there are three subgroups of mouse urine profiles in the APO E3 mouse cohort.

Figure 11:
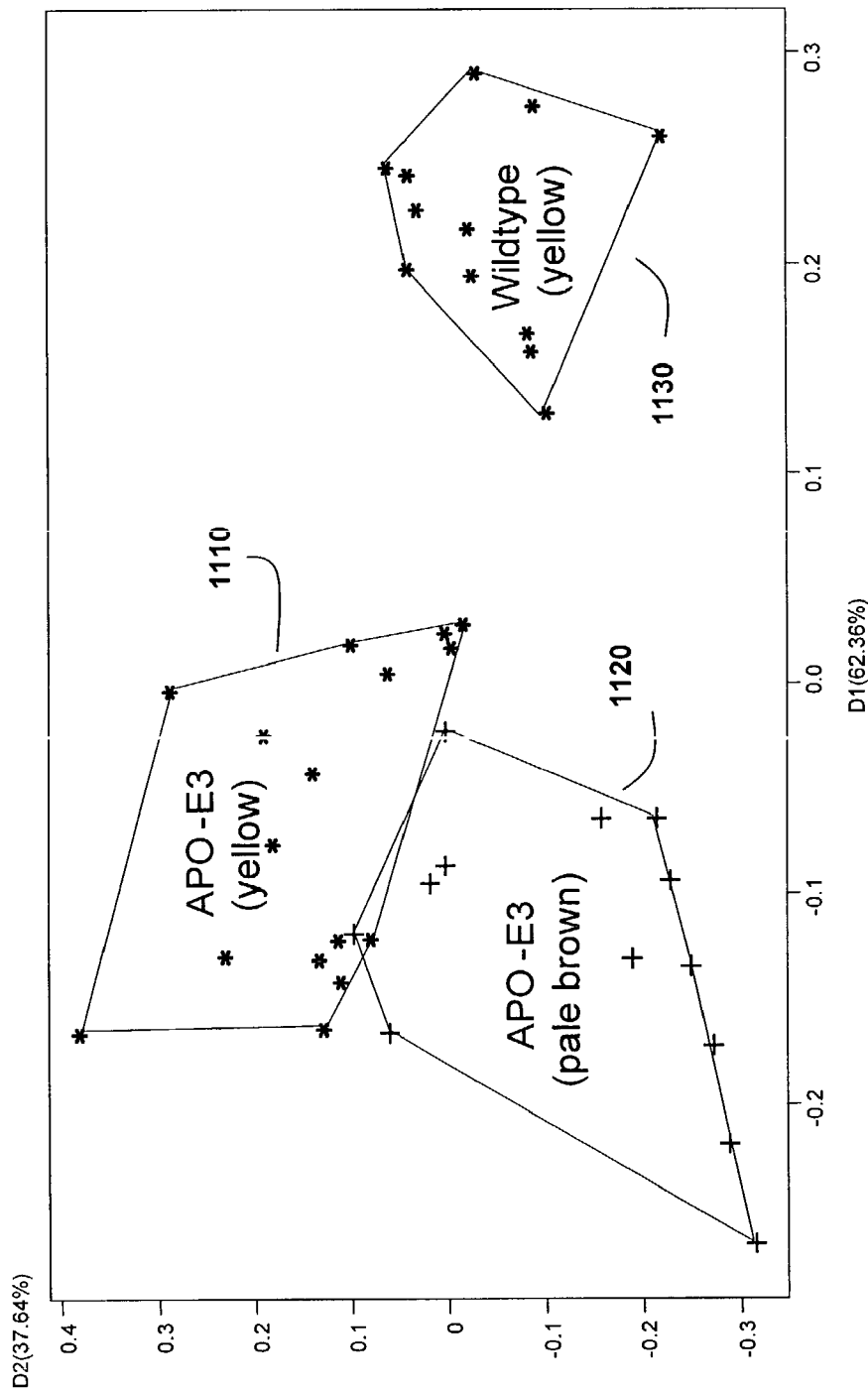
FIG. 11 is an example of a PCA-DA score plot of the NMR data for the urine samples of both wildtype and APO E3 mice.
Figure 12:
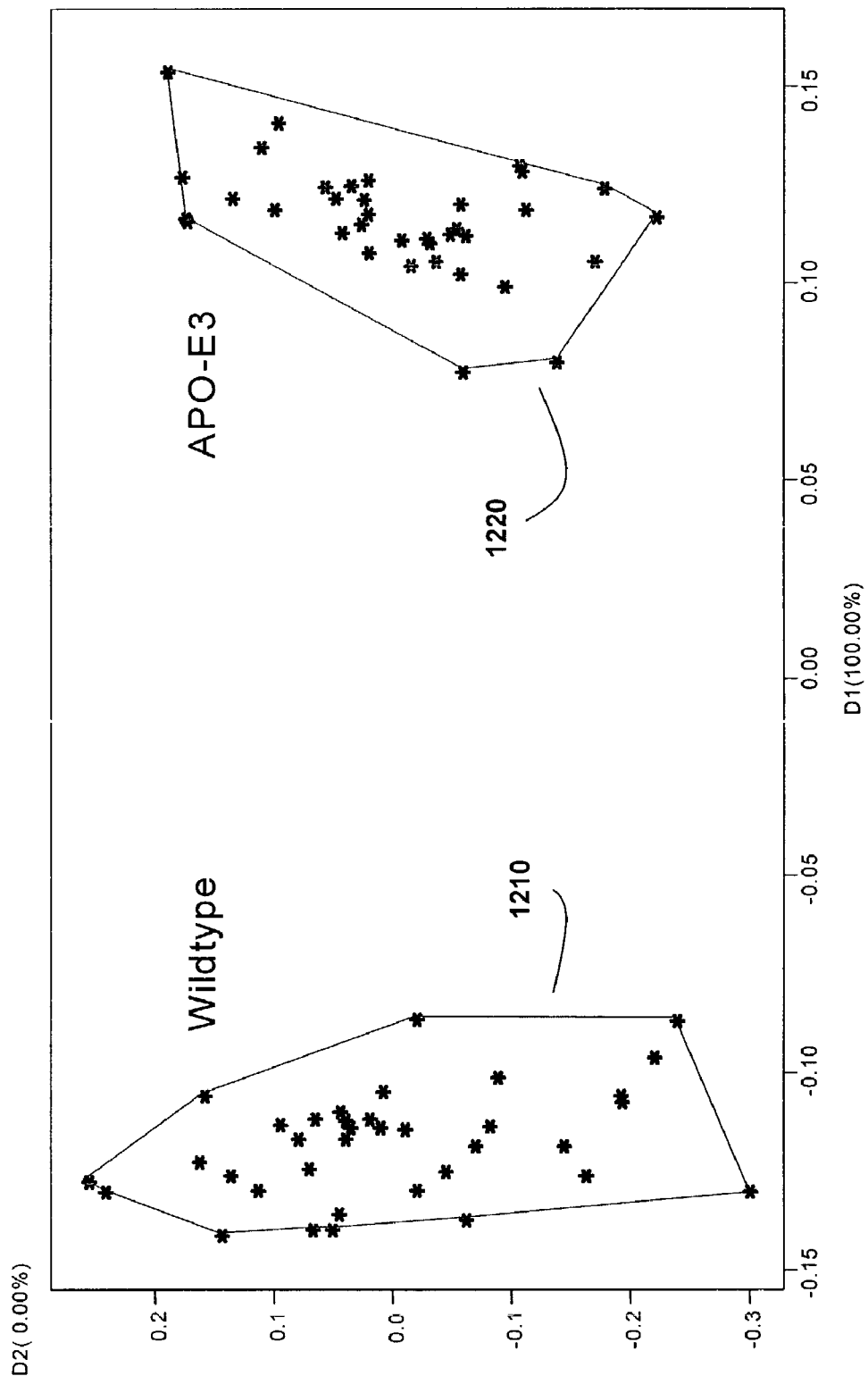
FIG. 12 is an example of a PCA-DA score plot of the NMR data for the blood plasma samples of data sets 3 and 4 of FIGS. 2A and 2B.

Referring to FIG. 11, a PCA-DA score plot of the NMR data for the urine samples of both wildtype and APO E3 mice is shown. As illustrated, the analysis indicates that there are similarities and differences within the urine samples of data sets 1 and 2 even for urine with the same color. Specifically, the analysis illustrates three regions in the score plot, one correlated to yellow APO E3 mouse urine 1110, one to pale brown APO E3 mouse urine 1120, and another to yellow wildtype mouse urine 1130. FIG. 11 illustrates that there are three distinct subgroups of mouse urine profiles which can be used as profiles to distinguish between APO E3 animals from wildtype animals, and to distinguish animals producing yellow urine from pale brown urine.

Referring to FIG. 12, a PCA-DA score plot of the NMR data for the blood plasma samples of data sets 3 and 4 is shown. As illustrated, the analysis groups NMR data for APO E3 and wildtype group into two substantially distinct regions in the score plot, a wildtype region 1210 and an APO E3 region 1220, indicating that blood samples alone may be suffice to develop a profile that distinguishes APO E3 mice from wildtype mice.

Figure 13:
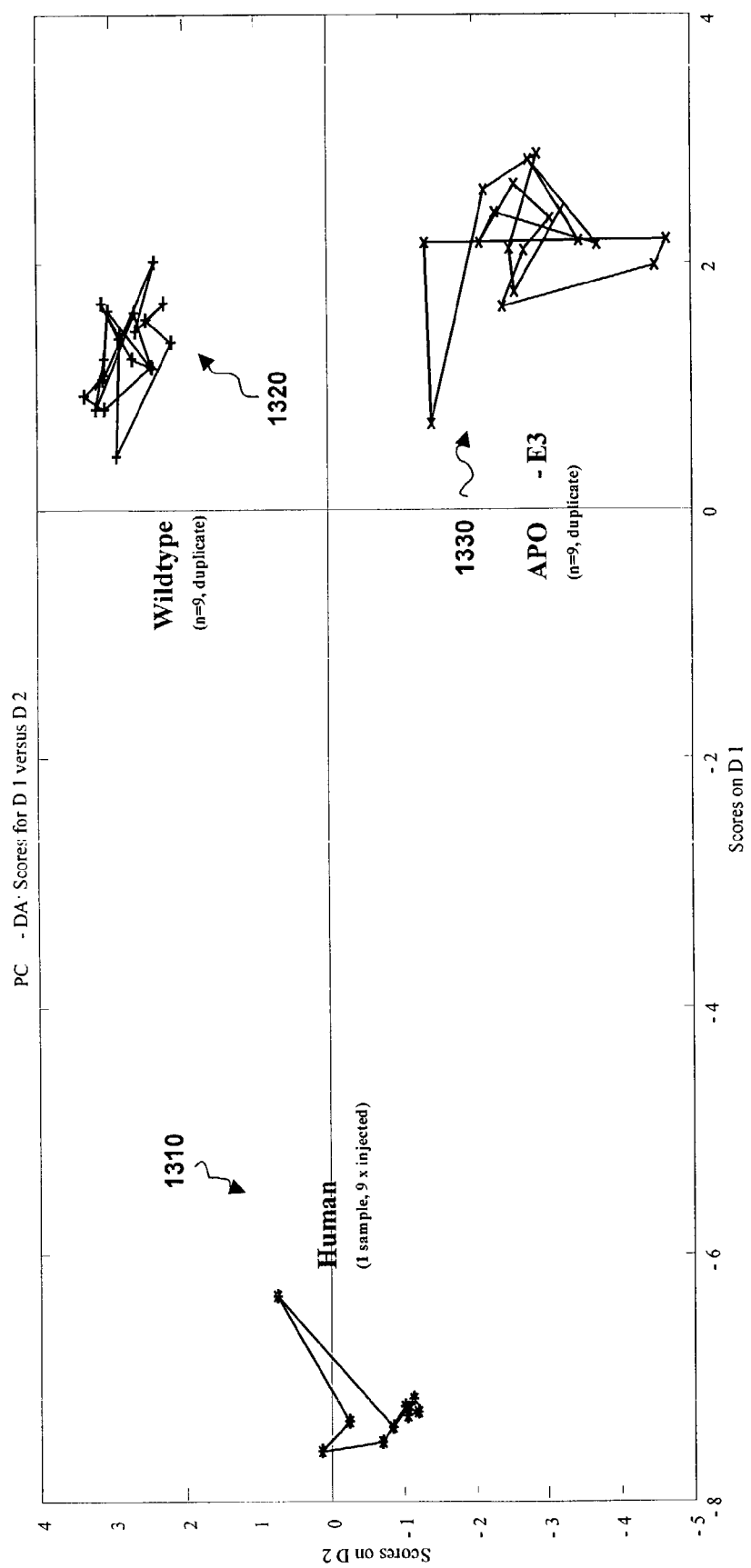
FIG. 13 is an example of a PCA-DA score plot of the LC-MS data on the blood plasma samples of data sets 5, 6 of FIGS. 2A and 2B and human samples.
Figure 14:
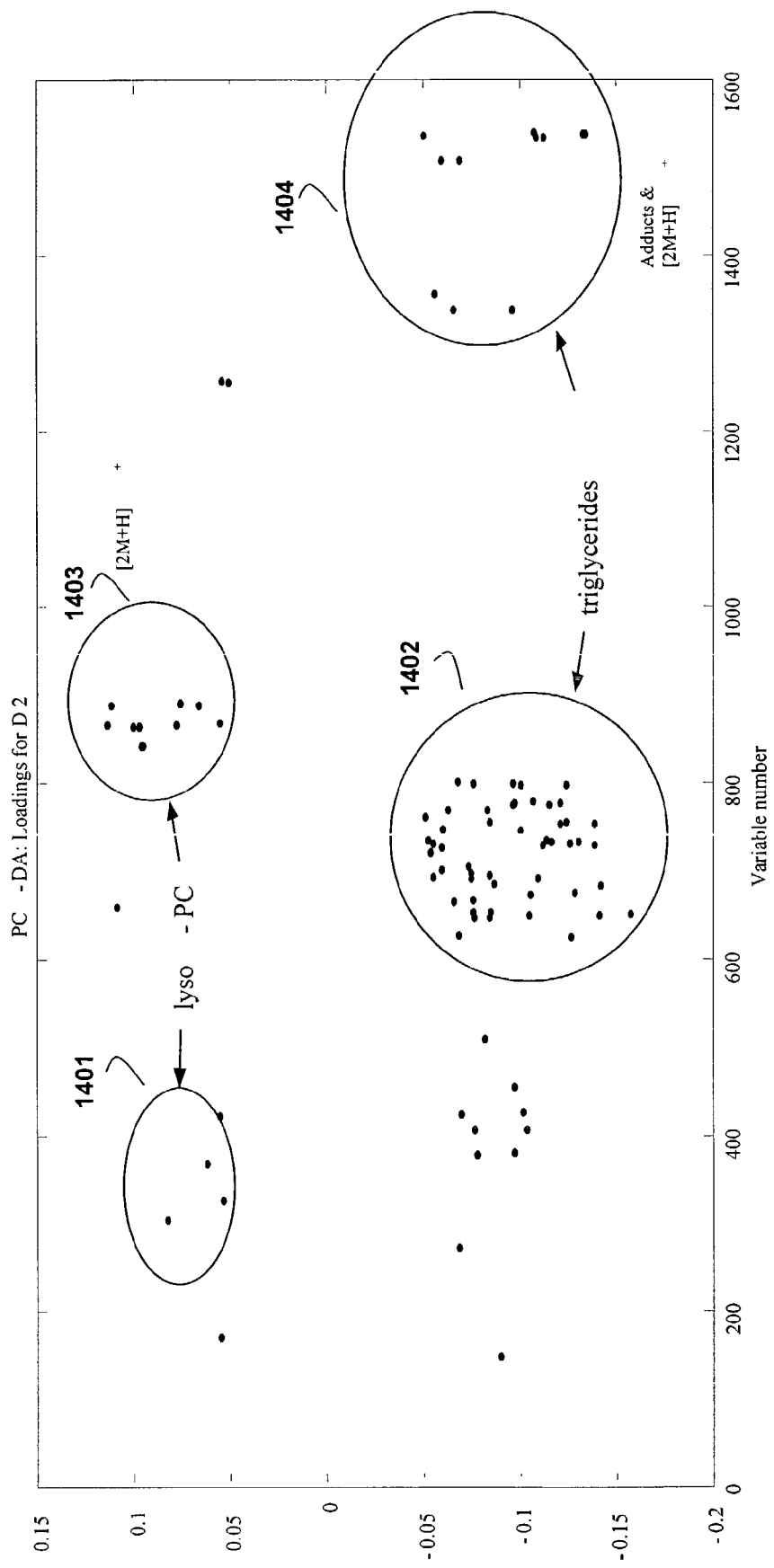
FIG. 14 is an example of a loading plot for axis D2 of FIG. 13.

Referring to FIG. 13, a PCA-DA score plot of the NMR data for the blood plasma samples of data sets 5, 6 and the human samples is shown. As illustrated, the analysis groups NMR data regions corresponding to each organism type, a human region 1310, a wildtype region 1320 and an APO E3 region 1330. FIG. 13 indicates that blood plasma samples may suffice to develop a profile that distinguishes organisms and genotypes. In one embodiment, information at a second level of correlation is obtained from the analysis illustrated in FIG. 13 to investigate, for example, the contribution of each metabolite measured by the NMR technique to the segregation of the data into three regions. In one version a loading plot is used to determine a second level of correlation. An example of a loading plot for axis D2 of FIG. 13 is shown in FIG. 14.

Referring to FIGS. 14 and 2A, four ranges of numbers are circled 1401-1404. The abscissa corresponds to masses (or mass-to-charge ranges). Points with positive values along the ordinate indicate component masses that are lower in abundance in the APO E3 mouse versus wildtype, and negative values indicate the reverse. As can be seen in FIG. 14, the circled ranges are a significant contribution to the correlations of, for example, FIG. 13. The mass chromatograms associated these regions were investigated 350 and the upper circled ranges 1401, 1403 found to be associated with lyso-phosphatidylcholines ("lyso-PC"), and the lower ranges 1402, 1404 with triglycerides. An example of the phosphatidylcholine mass chromatograms for both wildtype and APO E3 mouse are shown in FIG. 15, and an example of the lyso-phosphatidylcholine mass chromatograms for both wildtype and APO E3 mouse are shown in FIG. 16.

Figure 15:
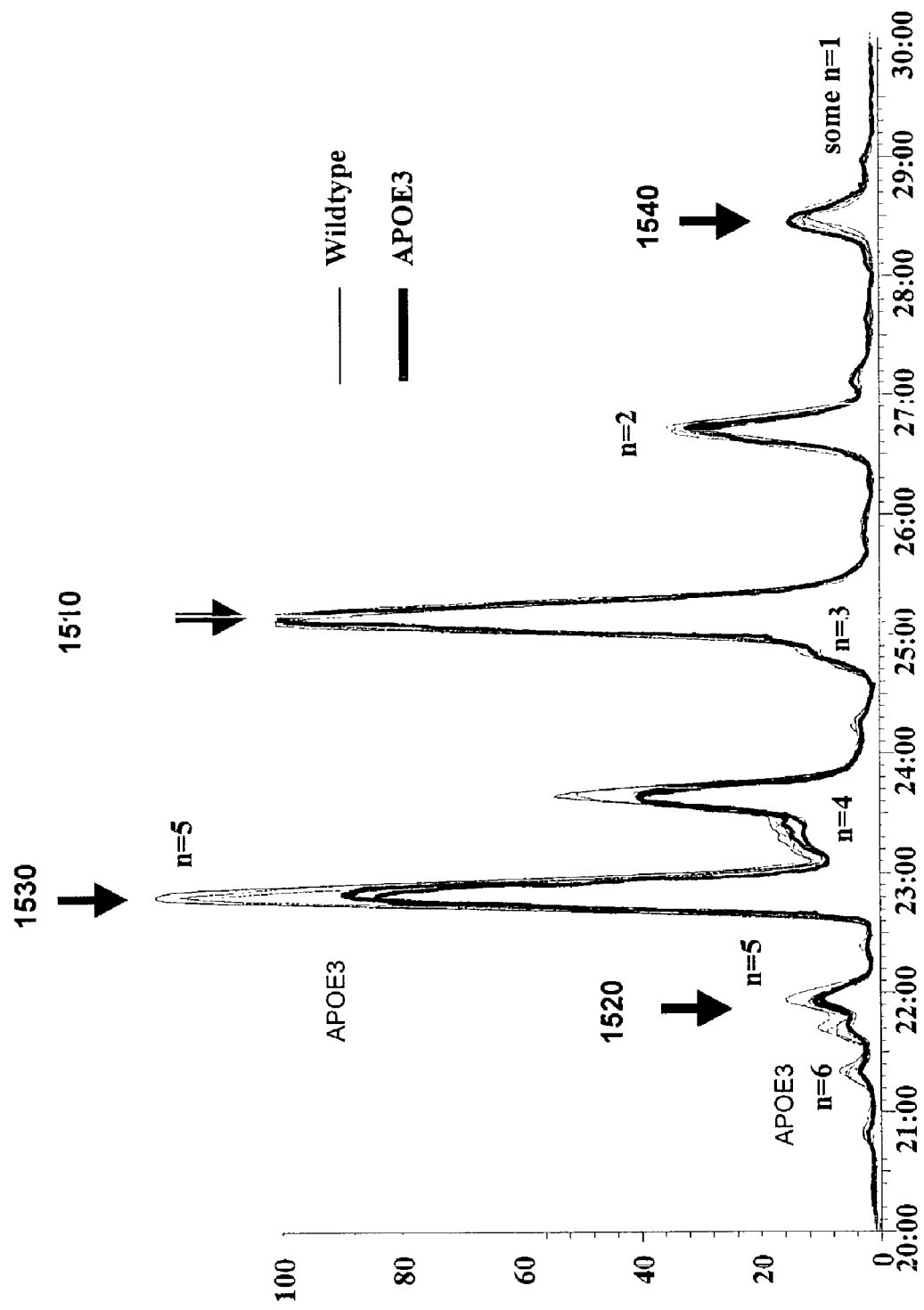
FIG. 15 is an example of the comparison of normalized blood plasma lipid profiles obtained by an LCMS spectrometric technique for wildtype mouse samples (thin sold line) and APO E3 mouse samples (thick sold line).

Referring to FIG. 15, a series of peaks corresponding phosphatidylcholines, where n refers to the number of residues, is shown for both wildtype (thin solid line) and APO E3 (thick solid line) plasma samples. The chromalograms in FIG. 15 are each normalized such that the maximum intensity of the n=3 peak 1510 is equal for all the spectra and it should be noted that although some n=1 is present, the majority of the signal corresponding to this peak location 1540 is not believed to arise from a phosphatidylcholine. As illustrated, it was observed that the peaks corresponding to n=5 1520, 1530 were substantially reduced in the APO E3 mouse spectra relative to wildtype.

Figure 16:
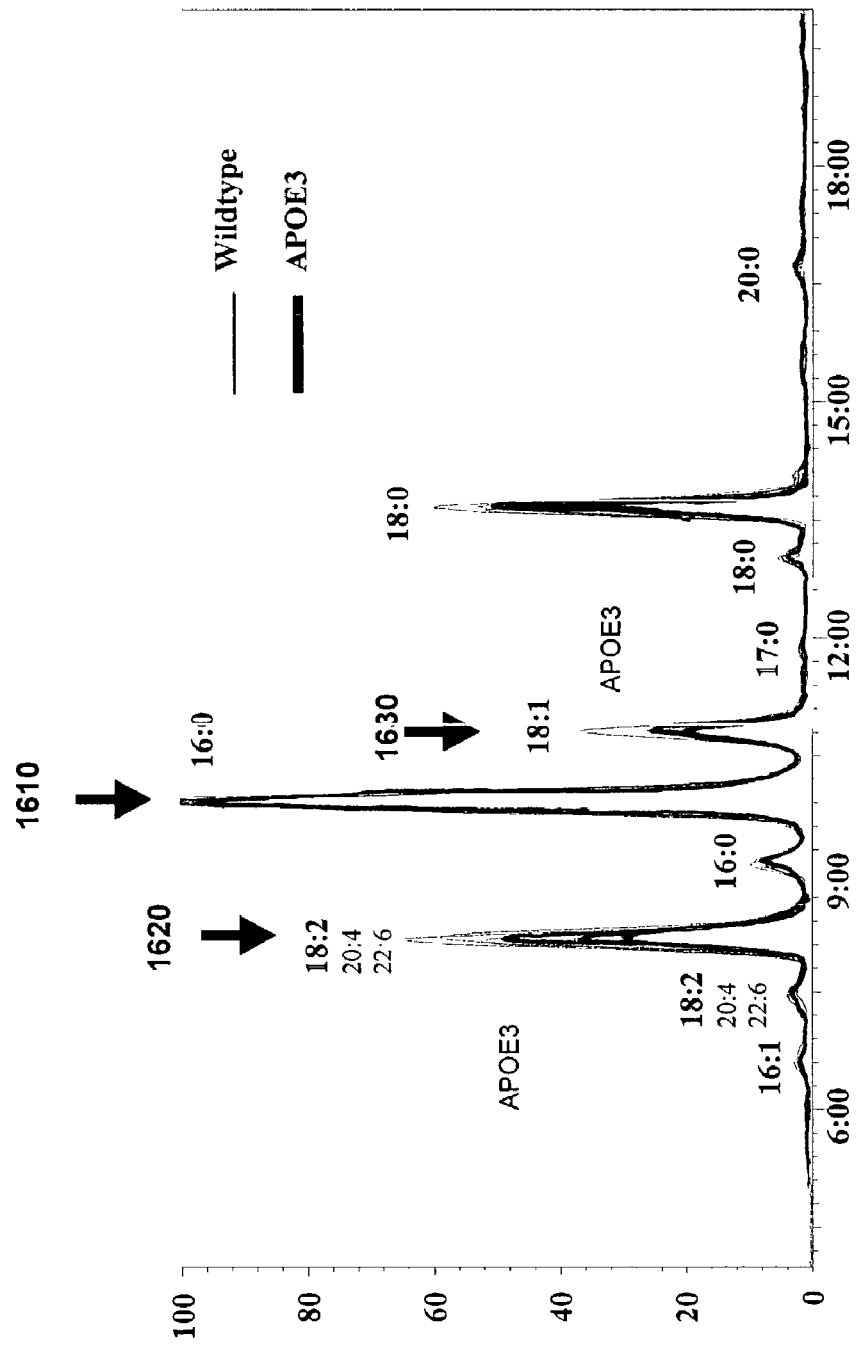
FIG. 16 is an example of the comparison of normalized blood plasma lipid profiles obtained by an LC-MS spectrometic technique for wildtype mouse samples (thin sold line) and APO E3 mouse samples (thick solid line).

Referring to FIG. 16, a series of peaks corresponding lyso-phosphatidylcholines, where the designation x:y refers to x number of carbon atoms on the fatty acids and y carbon bonds, is shown for both wildtype (thin solid line) and APO E3 (thick solid line) plasma samples. The chromatograms in FIG. 16 are each normalized such that the maximum intensity of peak 1610 is equal for all the spectra. As illustrated, it was observed that the peaks corresponding to arachidonic acid 1620, and linoleic acid 1630 were substantially reduced in the APO E3 mouse spectra relative to wildtype.

Figure 17:
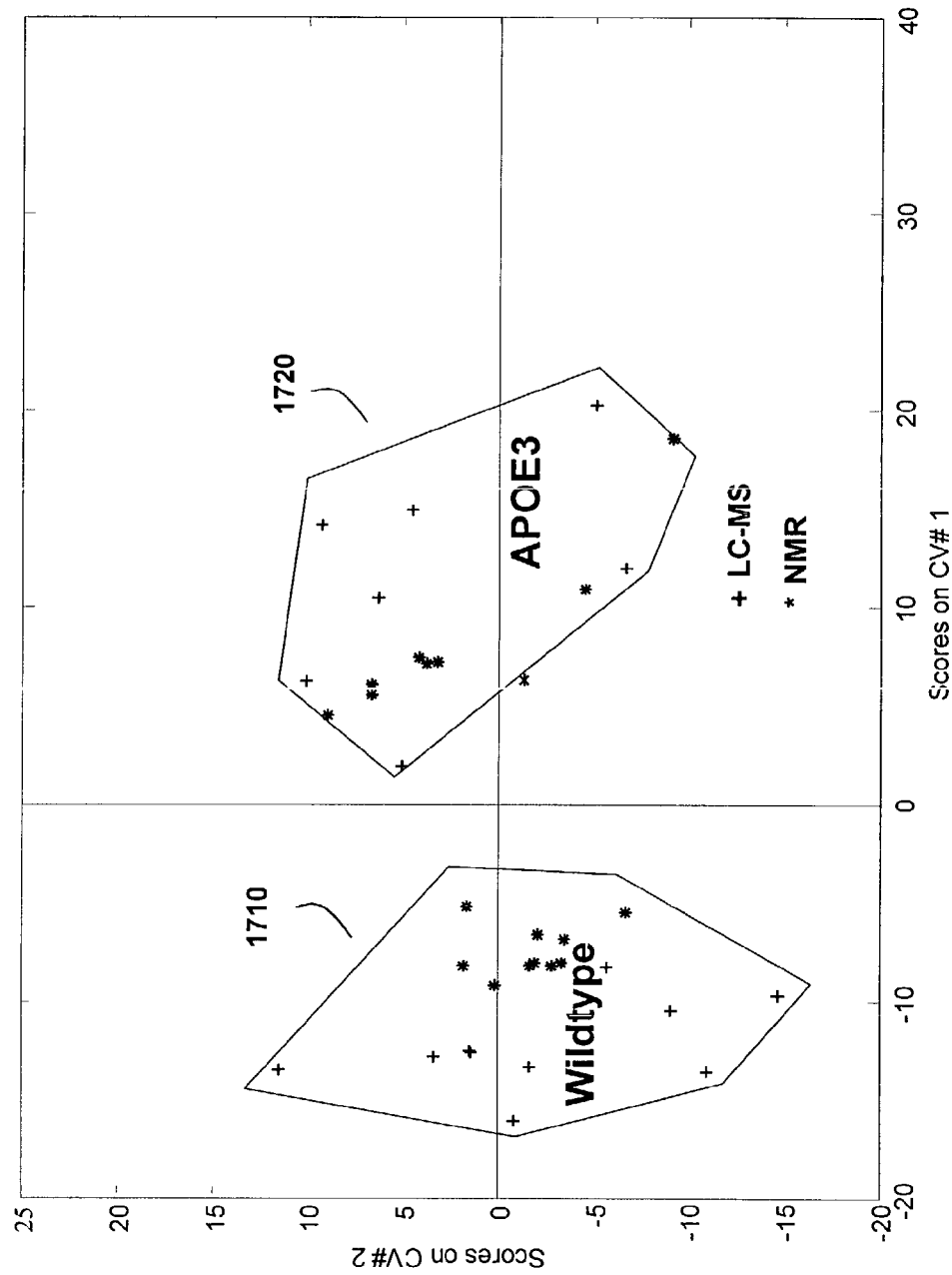
FIG. 17 is an example of a canonical correlation score plot for spectrometric data for one biological sample type (blood plasma) from two different spectrometric techniques (NMR and LC-MS).

Referring again to FIGS. 2A and 2B, a second multivariate analysis was also performed ("YES" to query 360) comprising a canonical correlation. This second multivariate analysis was performed on data sets 3, 4, 5, and 6, 371, to produce a canonical correlation score plot 381. An example of the results of this second multivariate analysis is shown in FIG. 17. It should be noted that analysis 371 correlates data from two very different spectrometric techniques: data sets 3 and 4 from NMR, and 5 and 6 from LC-MS. Such an analysis, for example, may discern whether different information is being provided by such different techniques.

As illustrated in FIG. 17, the canonical correlation groups both NMR and LC-MS results for the APO E3 mouse and wildtype mouse into two substantially distinct regions in the plot, a wildtype region 1710 and an APO E3 region 1720, indicating that both NMR and LC-MS techniques result in segregation into distinct regions, however the LC-MS method yielded a more pronounced separation.

Figure 18:
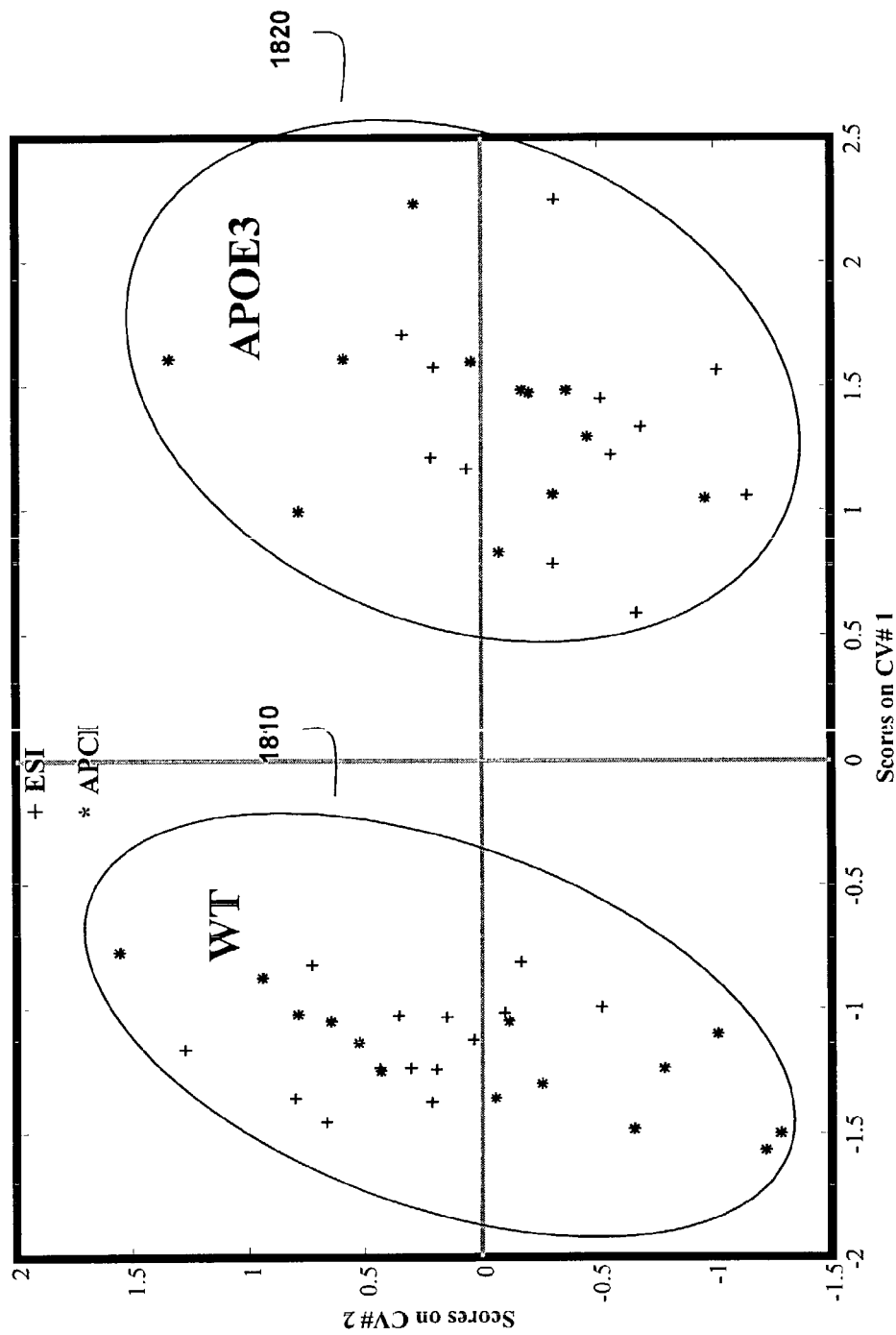
FIG. 18 is an example of a canonical correlation score plot for spectrometric data for one biological sample type (blood plasma) from the same general spectrometric technique but different instrument configurations.

A second multivariate analysis was performed on data sets 5, 6, 7 and 8, 372, to produce a canonical correlation score plot 382. An example of the results of this second multivariate analysis is shown in FIG. 18. It should be noted that analysis 372 correlates data from in many respects the same spectrometric technique LC-MS, but different instrument configurations: data sets 5 and 6 using ESI, and 7 and 8 using APCI. Such an analysis, for example, may discern whether different information is being provided by such different instrument configurations. In addition, such a multivariate analysis may be used to discern whether different machines (that use the exact same instrumentation) provide different information. In cases where different machines provide significantly different information (on the same sample, using the same technique, parameters, and instrumentation) user or machine errors may be detected.

As illustrated in FIG. 18, the canonical correlation groups both ESI LC-MS results (crosses +) and APCI LC-MS results (asterisks *) for the APO E3 mouse and wildtype mouse into two substantially distinct regions in the plot, a wildtype region 1810 and an APO E3 region 1820, indicating that both ESI LC-MS and APCI LC-MS techniques result in segregation into distinct regions.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method of profiling a state of a biological system in an animal, the method comprising:

evaluating with a suitably programmed computer a plurality of data sets with a multivariate analysis and correlating spectral features to generate a profile of one or more biomarkers in response to one or more correlations, the profile characterizing a state of the biological system, wherein the multivariate analysis comprises principal component analysis, and the plurality of data sets comprise at least two different types of spectrometric measurements of a sample of a biological system, wherein the spectrometric measurements are from more than one spectrometric technique comprising mass spectrometry, nuclear magnetic resonance spectrometry, liquid chromatography, gas chromatography, high performance liquid chromatography, or capillary electrophoresis; and displaying at least a portion of data relevant to the profile.

2. The method of claim 1, wherein the multivariate analysis further comprises at least one of discriminant analysis, principal component analysis with discriminant analysis, canonical correlation, kernel principal component analysis, non-linear principal component analysis, factor analysis, multidimensional scaling, and cluster analysis.

3. The method of claim 1, wherein the multivariate analysis comprises a hierarchical cascade of two or more multivariate analyses.

4. The method of claim 1, wherein the plurality of data sets are derived from a biological sample type selected from the group consisting of blood, blood plasma, blood serum, cerebrospinal fluid, bile, saliva, synovial fluid, pleural fluid, pericardial fluid, peritoneal fluid, feces, nasal fluid, ocular fluid, intracellular fluid, intercellular fluid, lymph fluid, and urine.

5. The method of claim 1, wherein the plurality of data sets are derived from a biological sample type selected from the group consisting of liver cells, epithelial cells, endothelial cells, kidney cells, prostate cells, blood cells, lung cells, brain cells, skin cells, adipose cells, tumor cells, and mammary cells.

6. The method of claim 1, wherein the sample comprises samples taken at different times for the same organism.

7. The method of claim 1, further comprising the step of comparing the profile to a database of profiles.

8. The method of claim 1, wherein evaluating comprises evaluating a quality factor for data sets of two or more spectrometric measurement techniques to determine differences arising from spectrometric measurement technique.

9. The method of claim 1, wherein the state of the biological system comprises a disease state.

10. The method of claim 1, wherein the state of the biological system comprises a response to a pharmacological agent.

11. The method of claim 1, wherein the state of the biological system comprises a response to at least one of age, environment, and stress.

12. An article of manufacture having a computer-readable medium with computer-readable instructions embodied thereon for performing the method of claim 1.

13. A system for profiling a state of a biological system in an animal, the system comprising:

(a) one or more spectrometric instruments adapted to provide at least one data set comprising at least two different types of spectrometric measurements of a sample of a biological system, wherein the spectrometric measurements are from at least two different spectrometric techniques comprising mass spectrometry, nuclear magnetic resonance spectrometry, liquid chromatography, gas chromatography, high performance liquid chromatography, or capillary electrophoresis; and (b) a data processing device in communication with the one or more spectrometric instruments, wherein the data processing device embodies logic adapted to (i) evaluate the at least one data set with a multivariate analysis and correlate spectral features to generate a profile of one or more biomarkers in response to one or more correlations, the profile characterizing a state of the biological system, wherein the multivariate analysis comprises principal component analysis.

14. The system of claim 13, wherein the system further comprises an external database accessible by the data processing device.

15. The method of claim 1 wherein the plurality of data sets is derived from one biological sample type.

16. The method of claim 1 wherein the plurality of data sets is derived from one biological sample type that is treated differently.

17. The method of claim 1 wherein the biological system is in an animal.

18. The method of claim 1, wherein the plurality of data sets comprise spectrometric measurements of a biomolecule component type.

19. The method of claim 18, wherein the biomolecule component type is a gene transcript, a protein, or a metabolite.

20. A method of profiling a state of a biological system in an animal, the method comprising:

analyzing a sample of a biological system to provide a plurality of data sets comprising at least two different types of spectrometric measurements obtained from at least two different spectrometric techniques comprising mass spectrometry, nuclear magnetic resonance spectrometry, liquid chromatography, gas chromatography, high performance liquid chromatography, or capillary electrophoresis; and evaluating with a suitably programmed computer the plurality of data sets with a multivariate analysis and correlating spectral features to generate a profile of one or more biomarkers in response to one or more correlations, the profile characterizing a state of the biological system, wherein the multivariate analysis comprises principal component analysis.

21. The method of claim 20, wherein the multivariate analysis further comprises at least one of discriminant analysis, principal component analysis with discriminant analysis, canonical correlation, kernel principal component analysis, non-linear principal component analysis, factor analysis, multidimensional scaling, and cluster analysis.

22. The method of claim 20, wherein the multivariate analysis comprises a hierarchical cascade of two or more multivariate analyses.

23. The method of claim 20, wherein the plurality of data sets are derived from a biological sample type selected from the group consisting of blood, blood plasma, blood serum, cerebrospinal fluid, bile, saliva, synovial fluid, pleural fluid, pericardial fluid, peritoneal fluid, feces, nasal fluid, ocular fluid, intracellular fluid, intercellular fluid, lymph fluid, and urine.

24. The method of claim 20, wherein the plurality of data sets are derived from a biological sample type selected from the group consisting of liver cells, epithelial cells, endothelial cells, kidney cells, prostate cells, blood cells, lung cells, brain cells, skin cells, adipose cells, tumor cells, and mammary cells.

25. The method of claim 20, wherein the sample comprises samples taken at different times for the same organism.

26. The method of claim 20, further comprising the step of comparing the profile to a database of profiles.

27. The method of claim 20, wherein evaluating comprises evaluating a quality factor for data sets of two or more spectrometric measurement techniques to determine differences arising from spectrometric measurement technique.

28. The method of claim 20, wherein the state of the biological system comprises a disease state.

29. The method of claim 20, wherein the state of the biological system comprises a response to a pharmacological agent.

30. The method of claim 20, wherein the state of the biological system comprises a response to at least one of age, environment, and stress.

31. The method of claim 20 wherein the plurality of data sets is derived from one biological sample type.

32. The method of claim 20 wherein the plurality of data sets is derived from one biological sample type that is treated differently.

33. The method of claim 20 wherein the biological system is in an animal.

34. The method of claim 20, wherein the plurality of data sets comprise spectrometric measurements of a biomolecule component type.

35. The method of claim 34, wherein the biomolecule component type is a gene transcript, a protein, or a metabolite.

36. An article of manufacture having a computer-readable medium with computer-readable instructions embodied thereon for performing the method of claim 20.

37. A method of profiling a state of an animal, the method comprising:
  evaluating with a suitably programmed computer a plurality of data sets with a multivariate analysis comprising principal component analysis and correlating spectral features to generate a profile of one or more biomarkers in response to one or more correlations, the profile characterizing a state of the animal,
  wherein the plurality of data sets comprise at least two different types of spectrometric measurements of a sample of an animal,
  the spectrometric measurements comprise measurements of a gene transcript, a protein, or a metabolite, and
  the spectrometric measurements are from more than one spectrometric technique comprising mass spectrometry, nuclear magnetic resonance spectrometry, liquid chromatography, gas chromatography, high performance liquid chromatography, or capillary electrophoresis; and
  displaying at least a portion of data relevant to the profile.

38. A method of profiling a state of an animal, the method comprising:
  analyzing a sample of an animal to provide a plurality of data sets, the plurality of data sets comprising at least two different types of spectrometric measurements obtained using at least two different spectrometric techniques comprising mass spectrometry, nuclear magnetic resonance spectrometry, liquid chromatography, gas chromatography, high performance liquid chromatography, or capillary electrophoresis, wherein the spectrometric measurements comprise measurements of a gene transcript, a protein, or a metabolite; and
  evaluating with a suitably programmed computer the plurality of data sets with a multivariate analysis comprising principal component analysis and correlating spectral features to generate a profile of one or more biomarkers in response to one or more correlations, the profile characterizing a state of the animal.

* * * * *